US012157873B2

(12) United States Patent
Brower et al.

(10) Patent No.: US 12,157,873 B2
(45) Date of Patent: Dec. 3, 2024

(54) SYSTEMS AND DEVICES FOR PRODUCING BIOLOGICAL PRODUCTS AND METHODS OF USING THE SAME

(71) Applicant: Genzyme Corporation, Cambridge, MA (US)

(72) Inventors: Kevin Brower, Holliston, MA (US); Michael Coolbaugh, Waltham, MA (US); Xhorxhi Gjoka, Worcester, MA (US); Chad Varner, Marlborough, MA (US); Jason Walther, Holliston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/374,435

(22) Filed: Sep. 28, 2023

(65) Prior Publication Data

US 2024/0101945 A1 Mar. 28, 2024

Related U.S. Application Data

(60) Provisional application No. 63/415,099, filed on Oct. 11, 2022, provisional application No. 63/410,878, filed on Sep. 28, 2022.

(51) Int. Cl.
*C12M 3/00* (2006.01)
*B01D 15/18* (2006.01)
(Continued)

(52) U.S. Cl.
CPC ......... *C12M 23/44* (2013.01); *B01D 15/1821* (2013.01); *B01D 15/3804* (2013.01); *C12M 47/10* (2013.01); *C12M 47/12* (2013.01)

(58) Field of Classification Search
None
See application file for complete search history.

(56) References Cited

U.S. PATENT DOCUMENTS 1,191,274 A 7/1916 Brayton
5,996,634 A 12/1999 Dennehey et al.
(Continued)

FOREIGN PATENT DOCUMENTS

EP 3845626 A1 7/2021
WO WO-2023154245 A2 * 8/2023
WO 2024/076757 A1 4/2024

OTHER PUBLICATIONS

Godawat et al. "End-to-end integrated fully continuous production of recombinantmonoclonal antibodies." Journal of Biotechnology 213 (2015) 13-19. (Year: 2015).*

(Continued)

*Primary Examiner* — William H. Beisner
(74) *Attorney, Agent, or Firm* — McCarter & English, LLP

(57) ABSTRACT

Systems and devices for producing biological products and methods of using the same are provided. An example universal skid includes a rigid support and a plurality of flow-channel hardware sets. Each flow-channel hardware set couples with a respective flow channel of a plurality of flow channels for unit operations. The flow-channel hardware sets allow the flow channels to operate in parallel or in series for continuous processing over the unit operations. An example modular assembly includes one or more single-use kits for one or more unit operations and a universal skid coupled with the one or more single-use kits. An example manufacturing system includes multiple modular assemblies coupled with each other allowing continuous processing within each modular assembly, in between the modular assemblies, fully continuous processing across multiple unit operations.

26 Claims, 32 Drawing Sheets

(51) Int. Cl.
*B01D 15/38* (2006.01)
*C12M 1/00* (2006.01)

(56) References Cited

U.S. PATENT DOCUMENTS

| | | | |
|---|---|---|---|
| 10,920,182 | B2 | 2/2021 | Warikoo et al. |
| 11,306,341 | B2 | 4/2022 | Hwang et al. |
| 11,369,703 | B2 | 6/2022 | Patil et al. |
| 11,391,725 | B2 | 7/2022 | Wang et al. |
| 11,440,010 | B2 | 9/2022 | Vetter et al. |
| 11,884,703 | B2 | 1/2024 | Vetter et al. |
| 2002/0128585 | A1 | 9/2002 | Cork et al. |
| 2008/0269468 | A1* | 10/2008 | Vogel .............. C07K 14/755 530/414 |
| 2017/0157566 | A1* | 6/2017 | Gefroh .............. B01D 61/145 |
| 2020/0299402 | A1 | 9/2020 | Brower et al. |
| 2020/0317728 | A1* | 10/2020 | Coolbaugh .......... C12P 21/005 |
| 2021/0033574 | A1 | 2/2021 | Heise et al. |
| 2022/0049206 | A1* | 2/2022 | Rathore ............. C12M 41/44 |
| 2023/0211260 | A1* | 7/2023 | Meyer .............. B01D 35/16 210/87 |
| 2023/0295224 | A1 | 9/2023 | Coolbaugh et al. |
| 2023/0340396 | A1 | 10/2023 | Lu et al. |
| 2023/0365946 | A1 | 11/2023 | Wasylenko et al. |

OTHER PUBLICATIONS

Joksch et al. "Smart Modular Package Units for Single-Use Processing." BioProcess International, 17(3) Mar. 2019, pp. 62-68. (Year: 2019).*

Lewa, "Lewa EcoPrime® Twin LPLC Multi-functional, twin column chromatography." Product Brochure (2018). (Year: 2018).*

Thakur et al."Automation of Dead End Filtration." Frontiers in Bioengineering and Biotechnology, Jul. 2020 | vol. 8 | Article 758, pp. 1-11. (Year: 2020).*

Verdot "Process-Scale Chromatography Process Chromatography Skid." Product Brochure, May 2015. (Year: 2015).*

Agilitech, Flexible Single-Use Technologies for Your Bioprocess, Shaped by you and poised to evolve. Retrieved online at: https://web.archive.org/web/20210929174035/https://agilitech.bio/bioprocess-single-use-systems/12 pages, Sep. 29, 2021.

Fujifilm, MaruX Continuous Biomanufacturing. Retrieved online at: https://web.archive.org/web/20200512080400/https://fujifilmdiosynth.com/cell-culture/marux-continuous-biomanufacturing/. 10 pages, May 12, 2020.

Pak Biosolutions, Driving Advancements in Biopharmaceutical MAnufacturing. Retrieved online at: https://web.archive.org/web/20211021204229/https://www.pakbiosolutions.com/. 3 pages, Oct. 21, 2021.

Pall, Allegro™ Connect Buffer Management System, Step by Step Guide. Biotech Instructions for use. Retrieved online at: https://www.pall.com/content/dam/pall/biopharm/regulatory/instructional-guides/allegro-connect-buffer-management-system-USD3416a-en.pdf. 88 pages, Jun. 2021.

Pharmaceutical Business Review, Novasep. Retrieved online at: https://web.archive.org/web/20200623004755/https://www.pharmaceutical-business-review.com/suppliers/novasep/. 7 pages, Jun. 23, 2020.

Sartorius, Resolute® BIoSMB PD System, Continuous Single-Use, Multicolumn Chromatography. Product Datasheet, retrieved online at: https://www.sartorius.com/download/699284/biosmb-pd-datasheet-en-b-2578756-sartorius-pdf-data.pdf. 3 pages, Feb. 2023.

Southey, Novasep launches Merck-tested BioSC Pilot for batch and continuous chromatography. BioPharmaReporter. Retrieved online at: https://www.biopharma-reporter.com/Article/2018/06/26/Novasep-launches-Merck-tested-BioSC-Pilot-for-batch-and-continuous-chromatography. 2 pages, Jun. 26, 2018.

International Search Report and Written Opinion for Application No. PCT/US2023/033980, dated Jan. 29, 2024, 11 pages.

* cited by examiner

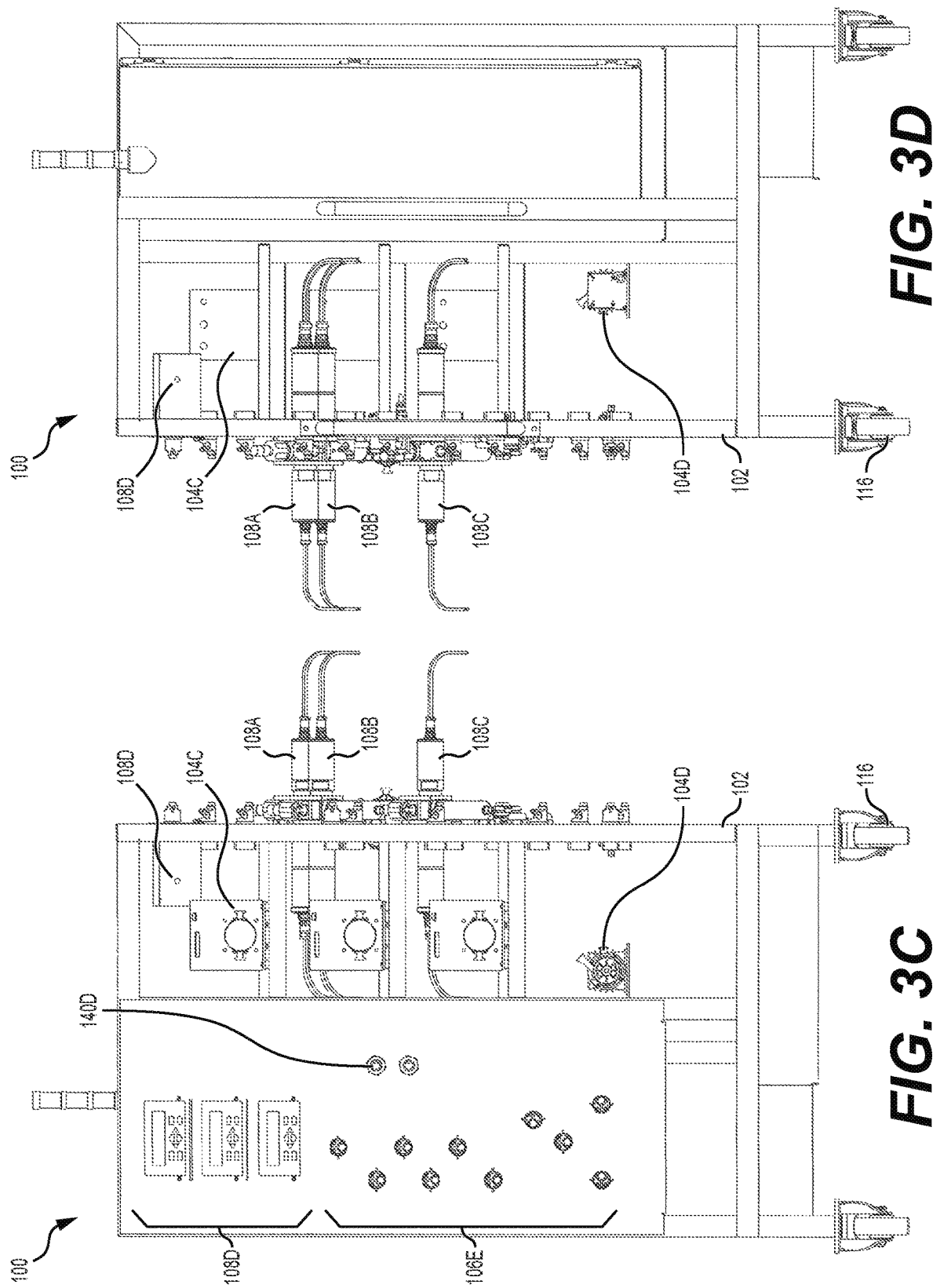

SYSTEMS AND DEVICES FOR PRODUCING BIOLOGICAL PRODUCTS AND METHODS OF USING THE SAME

CROSS-REFERENCE TO RELATED APPLICATION

This application claims the benefit of priority to U.S. Provisional Patent Application No. 63/410,878 filed on Sep. 28, 2022 and U.S. Provisional Patent Application No. 63/415,099 filed on Oct. 11, 2022, the entire contents of which are incorporated herein by reference.

BACKGROUND

Rapid advances in intensifying upstream processes for biologics production have left downstream processing as a bottleneck in the manufacturing scheme. Biomanufacturers are pursuing continuous downstream process development to increase efficiency and flexibility, reduce footprint and cost of goods, and improve product consistency and quality. However, the implementation of continuous downstream operations is limited due to different incompatible downstream unit operations (chromatography, inactivation, viral filtration, ultrafiltration/diafiltration), limited automation, limited operation range, large equipment size, increased service and maintenance, cost, and so forth. Thus, systems and devices for producing biological products and methods of using the same that address the foregoing, and other, needs are desired.

SUMMARY

The present disclosure provides systems and devices for producing biological products and methods of using the same. An example universal skid includes a rigid support and a plurality of flow-channel hardware sets. Each flow-channel hardware set couples with a respective flow channel for unit operations. The plurality of flow-channel hardware sets allow for continuous processing over the one or more unit operation. An example modular assembly includes one or more single-use kits for one or more unit operations and a universal skid coupled with the one or more single-use kits. An example manufacturing system includes multiple modular assemblies coupled with each other allowing continuous processing within each modular assembly, in between the multiple modular assemblies, fully continuous processing across multiple unit operations.

BRIEF DESCRIPTION OF THE DRAWINGS

The foregoing features of the present disclosure will be apparent from the following detailed description of the present disclosure, taken in connection with the accompanying drawings, in which:

FIG. 3C is a left view of the example universal skid of FIG. 3A.

FIG. 3D is a right view of the example universal skid of FIG. 3A.

DETAILED DESCRIPTION

Figure 1:
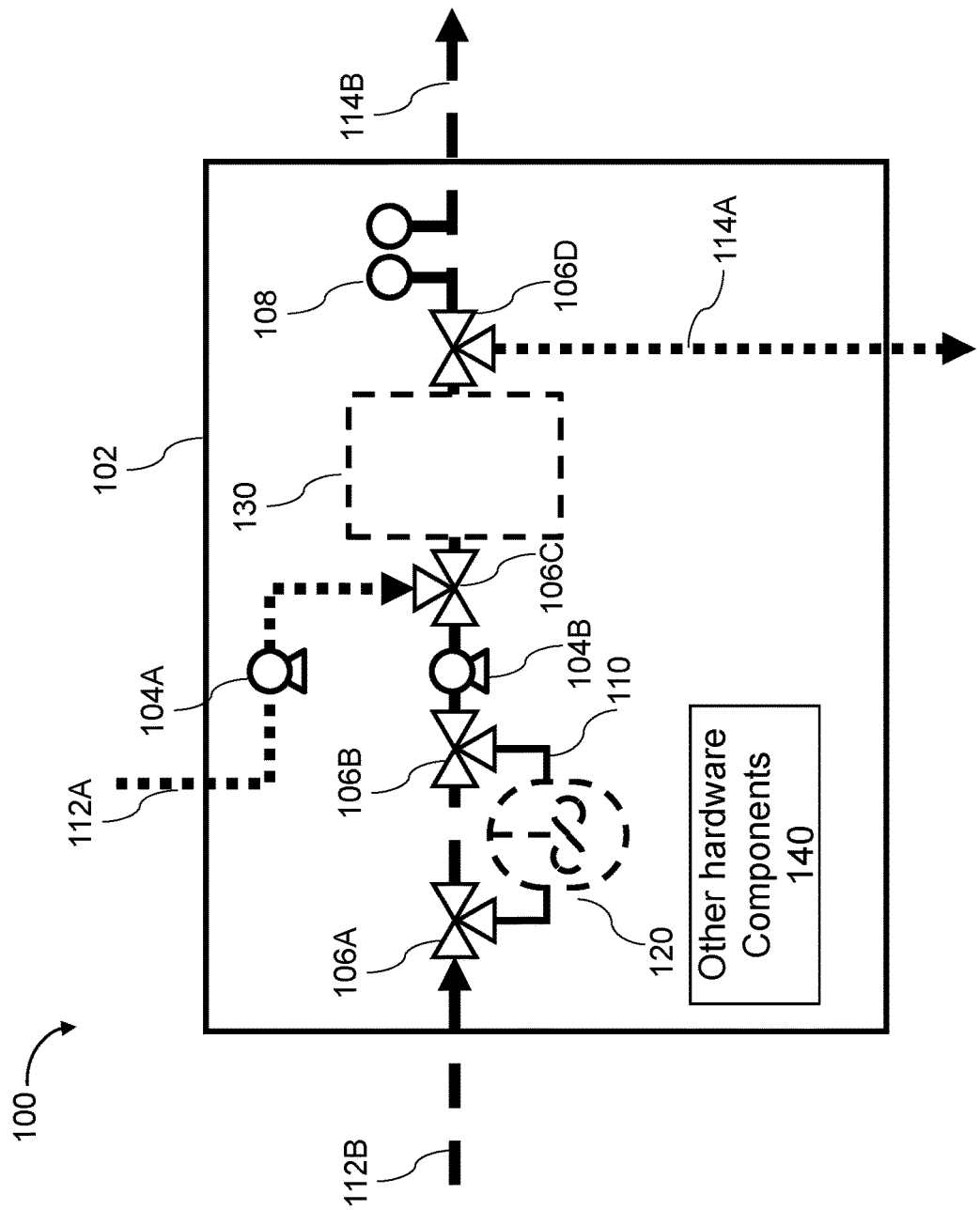
FIG. 1 is a diagram illustrating an example universal skid in accordance with some embodiments.

While various embodiments of the present disclosure have been shown and described herein, it will be obvious to those skilled in the art that such embodiments are provided by way of example only. Numerous variations, changes, and substitutions may occur to those skilled in the art without departing from the invention. It may be understood that various alternatives to the embodiments of the present disclosure described herein may be employed.

Reference will now be made in detail to certain exemplary embodiments according to the present disclosure, certain examples of which are illustrated in the accompanying drawings. Wherever possible, the same reference numbers will be used throughout the drawings to refer to the same or like parts.

As used in the specification and claims, the singular form "a," "an," and "the" include plural references unless the context clearly dictates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The present disclosure relates generally to the field of biomanufacturing and bioprocessing. More specifically, the present disclosure relates to systems and devices (e.g., manufacturing systems and/or devices using universal skids) for producing biological products and methods of using the same.

Continuous manufacturing is a routine way of production for industries such as petrochemical and food production. However, it has not been widely implemented in the biopharmaceutical industry. Because the technological needs for upstream and downstream development in biopharmaceuticals are different than those of other industries, the experience with continuous downstream operations is limited. Thus, there remains a need for a system that can accommodate different unit operations to provide continuous processing, which provides steady state operation, reduced equipment size, high-volumetric productivity, streamlined process flow, low-cycle times, and/or reduced capital cost.

Embodiments of the present disclosure provide a universal skid (as defined below) to accommodate different unit operations (as defined below), and integrate and/or connect flow paths of the different unit operations to perform continuous processing (as defined below). For example, a universal skid can include flow-channel hardware sets (as defined below) to support (via coupling, connecting, mounting, assembling, and/or the like) multiple flow channels of one or more single-use kits (as defined below) for one or more unit operations. Each flow-channel hardware set can support an individual flow channel (as defined below). The flow-channel hardware sets can be arranged in parallel or in series, or in other suitable arrangements, and/or in various combinations thereof to allow flow channels to operate in parallel, in series, and/or some combinations thereof. In some embodiments, flow-channel hardware sets can be identical or can have at least two same type of hardware components. In some embodiments, flow-channel hardware sets can be different. For example, one flow-channel hardware set can include more hardware components than another flow-channel hardware set.

In some embodiments, flow-channel hardware sets can allow flow channels to operate in parallel, to be switchable, and/or to be replaceable. For example, if a flow-channel hardware set for one flow channel is occupied (e.g., for processing biological samples or for buffer flow), another flow-channel hardware set can support an additional flow channel to perform the same processing step in parallel (e.g., for the same unit operation) or perform a different processing step in parallel (e.g., for a different unit operation). If a flow-channel hardware set for a flow channel fails to operate, that flow channel can switch to another flow-channel hardware set for processing. If a flow channel fails to operate, another flow channel can replace the failed flow channel by coupling to another flow channel hardware set. In such a way, instead of batch processing, universal skid(s) can allow continuous processing between an inlet and an outlet of a single universal skid and/or between an inlet and an outlet of a single-use kit for a single unit operation. Examples of a universal skid are described with respect to FIGS. 1-8. Instead of batch processing, universal skids can also allow fully continuous processing and/or end-to-end continuous processing across multiple unit operations. Examples of universal skids are described with respect to FIGS. 9-10.

In some embodiments, flow-channel hardware sets can allow flow channels to operate in series to perform continuous processing over a specific unit operation and/or across multiple unit operations. For example, flow channels can be coupled to flow-channel hardware sets of a universal skid and can operate in series to perform different processing steps such that fluid continuously flows into the flow channels to be processed for a specific unit operation and/or across multiple unit operations. In another example, flow channels can be coupled to flow-channel hardware sets of each of multiple universal skids and can operate in series such that fluid continuously flows into the flow channels to be processed for a specific unit operation and/or across multiple unit operations. In some embodiments, continuous processing over a specific unit operation and/or across multiple unit operations can be performed using a single universal skid or using multiple universal skids based on the in-series and/or in-parallel flow channels.

In some embodiments, at least by allowing continuous processing for a specific unit operation and/or multiple unit operations as described above, universal skids can cause zero, reduced, or optimized (e.g., minimal) hold-up volume for a specific unit operation and/or multiple unit operations, zero, reduced, or optimized (e.g., minimal) mean residence time in one or more surge vessels and/or one or more flow channels used (as defined below), and/or zero, reduced, or optimized (e.g., minimal) volume of one or more surge vessels and/or one or more flow channels used. For example, mean residence time of one or more surge vessels and/or one or more flow channels used can be less than about 30 minutes (e.g., about 10 minutes to about 30 minutes). In another example, mean residence time of one or more surge vessels and/or one or more flow channels can be less than about 60 minutes (e.g., about 40 minutes to about 60 minutes). In some embodiments, mean residence time of one or more surge vessels and/or one or more flow channels can be less than about 120 minutes. The shortened or limited mean residence time can cause a reduction in the hold-up volume and volume of one or more surge vessels and/or one or more flow channels used. Further, at least because of reduction in mean residence time, universal skids can allow one or more surge vessels to receive and send flow at the same time, and/or more flexible use of surge vessels (e.g., allowing use of different quantities, different sizes, different arrangements, or different volumes of surge vessels).

Embodiments of the present disclosure also provide a manufacturing system having a compact size in which universal skids at different scales are combined with different single-use kits to perform a continuous manufacturing across various unit operations to produce biological products (e.g., recombinant proteins, or other suitable biological products) in an automated manner. Examples of the manufacturing system are described with respect to FIGS. 9-10.

The present disclosure provides several technical benefits, including but not limited to one or more of: continuous processing for a single unit operation, fully continuous processing and/or end-to-end continuous processing across multiple unit operations, parallel processing, steady state operation, reduced number of skids used, reduced number and volumes of surge vessels used, reduced mean residence time of surge vessels used, reduced hold-up volumes, reduced overall size of a system/device for biomanufacturing, reduced capital cost, reduced service and maintenance, reduced complexity, simplified equipment qualification, simplified skid manufacturing, and so forth.

As used herein, a "unit operation" refers to a functional step that can be performed in a method of manufacturing a biological product, or a component of a system used in a process of manufacturing a biological product. For example, a unit operation can include filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the biological product, and removing unwanted salts. Examples of the unit operation can include methods and/or system components for chromatography (e.g., multi-column chromatography or other suitable chromatography), virus inactivation, virus filtration, ultrafiltration, diafiltration, ultrafiltration/diafiltration, formulation, sterile filtration, or another suitable functional step that can be performed in a method or a system of manufacturing a biological product, a recombinant protein, or the like.

As used herein, a "single-use kit" refers to a kit providing a collection of consumable and/or disposable components to perform a specific unit operation. Examples of the consumable and/or disposable components can include one or more surge vessels, one or more flow path elements (e.g., tubing, fluid conduits, pipelines, or the like), one or more columns, one or more filters, one or more chambers, one or more pump heads, one or more sensors, or other suitable disposable and/or consumable components needed for performing a specific unit operation.

As used herein, a "universal skid" refers to a three-dimensional solid structure that can act as a platform or support for various single-use kits to perform various unit operations described herein. A universal skid can, if it comprises one or more structures that enable movement (e.g., wheels, rollers, or the like), confer mobility on the manufacturing system or a portion thereof. A universal skid can include a plurality of hardware components including but not limited to pumps, valves, sensors, scales, regulators, flowmeters, and/or other suitable hardware that is configured to support a single-use kit and/or configured to couple with the disposable or consumable components of a single-use kit. A universal skid can be a single solid structure (e.g., all of its hardware components are mounted on the same cart). A universal skid can include multiple solid structures. For example, a universal skid can include multiple carts, each cart having some of hardware components. All or some of hardware components of a universal skid can be designed to support various single-use kits for the same or different unit operations. All or some of hardware components of a universal skid can be permanently mounted.

As used herein, a "flow channel" refers to part of a single-use kit as described above. An example flow channel can include one or more columns, one or more filters (e.g., for the purposes of ultrafiltration, diafiltration, sterile filtration, viral filtration, etc.), one or more viral inactivation chambers, flow path elements, other suitable disposable and/or consumable components associated with one or more unit operations, and/or some combinations thereof.

As used herein, a "flow-channel hardware set" refers to a set of hardware components of a universal skid to support a flow channel. Examples of a flow-channel hardware set can include pumps, valves, sensors, mounting hardware, and/or other suitable hardware components to support a flow channel.

As used herein, a "modular assembly" refers to an assembly having a universal skid coupled with one or more single-use kits for one or more unit operations. In some embodiments, a modular assembly can be an assembly having a universal skid coupled with a single-use kit for a specific unit operation. In some embodiments, a modular assembly can be an assembly having a universal skid coupled with multiple single-use kits for multiple unit operations.

As used herein, a "surge vessel" refers to a container to hold liquid and/or liquid mixture to absorb or manage flow rate fluctuations coming from an upstream process and/or keep the flow rate to a downstream process more constant or consistent. For example, a surge vessel can be placed between two unit operations, and/or at a downstream end of a feed line of a unit operation.

As used herein, "residence time" refers to total time that fluid has spent inside one or more surge vessels and/or one or more flow channels. Residence time can be a volume of one or more surge vessels and/or one or more flow channels divided by a flow rate. "Mean residence time" refers to average total time that fluid has spent inside one or more surge vessels and/or one or more flow channels over a predetermined time period.

As used herein, "continuous processing" or "continuous manufacturing" refers to bioprocessing in which a fluid is continuously fed through at least a part of a modular assembly for a specific unit operation and/or a fluid continuously flowing and being processed across modular assemblies for different unit operations from end to end. A unit operation is continuous if a corresponding modular assembly is capable of processing a continuous flow input for prolonged periods of time. A continuous unit operation has a zero, reduced, or optimized (e.g., minimal) internal hold-up volume within the corresponding modular assembly and/or a unit operation, zero, reduced, or optimized (e.g., minimal) mean residence time of one or more surge vessels used and/or one or more flow channels used, and/or zero, reduced, or optimized (e.g., minimal) volume of one or more surge vessels used and/or one or more flow channel used. The output can be continuous or discretized in small packets produced in a cyclic manner. Fully continuous processing is continuous processing over all unit operations—for example enabling all unit operations in the process to be operated simultaneously, with a consistent average flow of material between all of the unit operations. (This could be achieved, for example, by connecting multiple universal skids in series). Different unit operations are fully continuous if the integrated (physically connected or coupled) modular assemblies have zero, reduced, or optimized (e.g., minimal) hold-up volume in between and/or within the modular assemblies and/or multiple unit operations, zero, reduced, or optimized (e.g., minimal) mean residence time of one or more surge vessels used, and/or zero, reduced, or optimized (e.g., minimal) volume of one or more surge vessels and/or flow channels used.

As used herein, a "biological product" refers to one of a protein-based therapeutic substance, a nucleic acid-based drug substance, and a gene therapy drug substance. The protein-based therapeutic substance can include at least one of a protein, a peptide, an antibody, and an enzyme. The nucleic acid-based drug substance can include at least one of DNA, a plasmid, an oligonucleotide, an aptamer, a DNAzyme, an RNA aptamer, an RNA decoy, a microRNA fragment, a small interfering RNA fragment, lipid nanoparticles, vaccines, cell therapy and the like As used herein, a "recombinant protein" refers to an immunoglobulin, protein fragment, engineered protein, blood factor, nanobody, or enzyme, including an antibody or antibody fragment therefore.

Universal Skid and Modular Assembly for Various Unit Operations

Turning to the drawings, FIG. 1 is a diagram illustrating an example universal skid 100 of the present disclosure. The universal skid 100 includes a support 102, a plurality of pumps 104, a plurality of valves 106, a plurality of sensors 108, a surge vessel support 110 to support a surge vessel 120, a plurality of inlets 112, a plurality of outlets 114, and other hardware components 140 (e.g., regulators, flowmeters, power supply, mounting hardware, scale to measure a weight of a surge vessel 120, or other suitable hardware components for monitoring, measuring, supporting, coupling, connecting, and/or communicate with a single-use kit 130). The universal skid 100 can further be coupled with a single-use kit 130 to perform a specific unit operation. The single-use kit 130 can be easily assembled and/or disassembled with the universal skid 100 as further described with respect to FIGS. 2-8.

The support 102 (e.g., a rigid casting, a movable cart, or the like) is configured to support hardware components of the universal skid 100. The hardware components of the universal skid 100 can be mounted on the support 102. The support 102 can also include one or more structures that enable movement (e.g., wheels, rollers, or the like).

The pumps 104 are configured to pump/pressurize a liquid (e.g., buffer) and/or a liquid mixture (e.g., a biological sample, a processed biological sample, waste or the like). The pumps 104 can be in communication with flow path elements (e.g., tubing, fluid conduits, pipelines, or the like) of the single-use kit 130 by compressing the flow path elements in such a manner that the liquid mixture is pressurized, thereby causing an output fluid flow from the pumps 104. For example, the pump 104A can be configured to pump/pressurize a buffer flowing into the universal skid 100 via an inlet 112A (e.g., a place or means for entering the universal skid 100). The pump 104B can be configured to pump/pressurize a biological sample from an inlet 112B flowing into the single-use kit 130 via the valve 106C. The pumps 104 can include various types of pumps to pump/pressurize the liquid or the liquid mixture, such as centrifugal pumps, peristaltic pumps, diaphragm pumps, and/or other pump mechanisms to pump/pressurize the liquid and/or liquid mixture.

The valves 106 are configured to control fluid flows entering and/or exiting one or more components of the universal skid 100, the single-use kit 130, and/or another universal skid. For example, the valve 106A can control a fluid flow (e.g., a biological sample flowing into the universal skid 100 via the inlet 112B) entering the surge vessel 120 and/or entering another valve 106B that controls a fluid flow entering the pump 104B. The valve 106C can control a fluid flow entering the single-use kit 130. The valve 106D can control a fluid flow exiting the universal skid 100 via the outlet 114A and 114B (e.g., an outlet refers to a place or means for exiting the universal skid 100).

The sensors 108 are configured to monitor the bioprocessing operation upstream and downstream of the outlets 114 and/or the inlets 112. Example sensors can include flow sensors, ultraviolet sensors, conductivity sensors, pH sensors, index of refraction sensors, pressure sensors, or other suitable sensors to detect data/signals associated with the universal skid 100.

Figure 2:
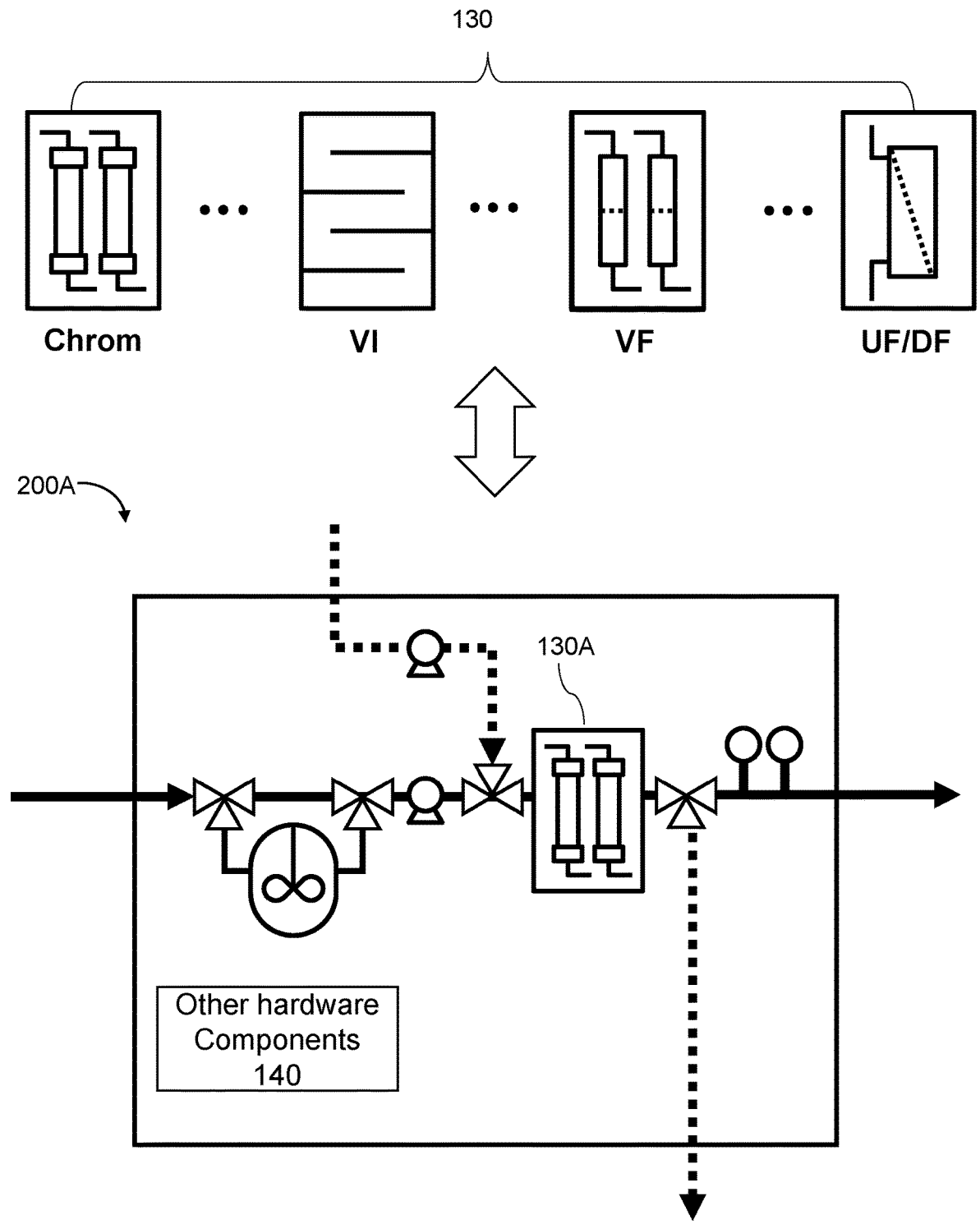
FIG. 2 is a diagram illustrating an example modular assembly in accordance with some embodiments.

FIG. 2 is a diagram illustrating an example modular assembly 200 of the present disclosure. The modular assembly 200 can be a universal skid 100 coupled (e.g., assembled, connected, mounted, or inserted) with a specific single-use kit 130 for chromatography (Chrom), virus inactivation (VI), viral filtration (VF), ultrafiltration/diafiltration (UF/DF), and other suitable unit operations. As illustrated in FIG. 2, for illustration purposes, a modular assembly 200A is a universal skid 100 assembled with a specific single-use kit 130A for chromatography. It should be understood that a universal skid 100 can be coupled with one or more of any other single-use kits 130 (e.g., a kit for VI, VF, or UF/DF) to form a modular assembly 200.

In some embodiments, a unit operation can be a component of a system used in a process of biomanufacturing. The modular assembly 200 can be coupled with one or more components of one or more operation units. Examples of a unit operation can include a unit operation having a bioreactor comprising host cells that produce a recombinant protein or the like, a unit operation comprising one or more capture chromatography systems, a unit operation having one or more post-capture chromatography systems, a unit operation having an ultrafiltration system and diafiltration system, a unit operation located between the above-noted operation units (e.g., a subsystem for performing virus inactivation, a second subsystem for performing virus filtration, in-line excipients for formulating a therapeutic drug substance), or some combinations thereof.

Figure 3A:
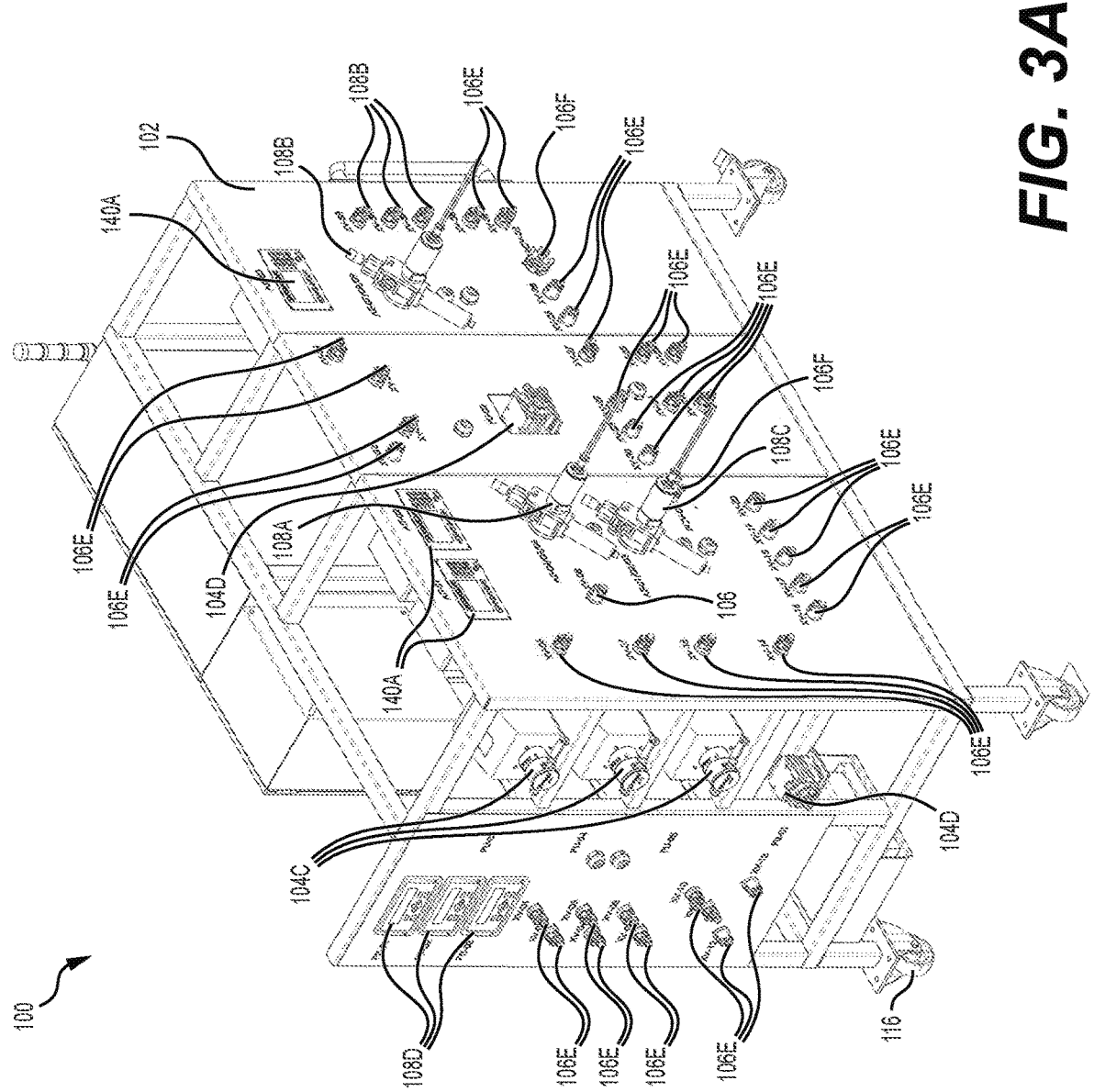
FIG. 3A is a perspective view of an example universal skid in accordance with some embodiments.
Figure 3B:
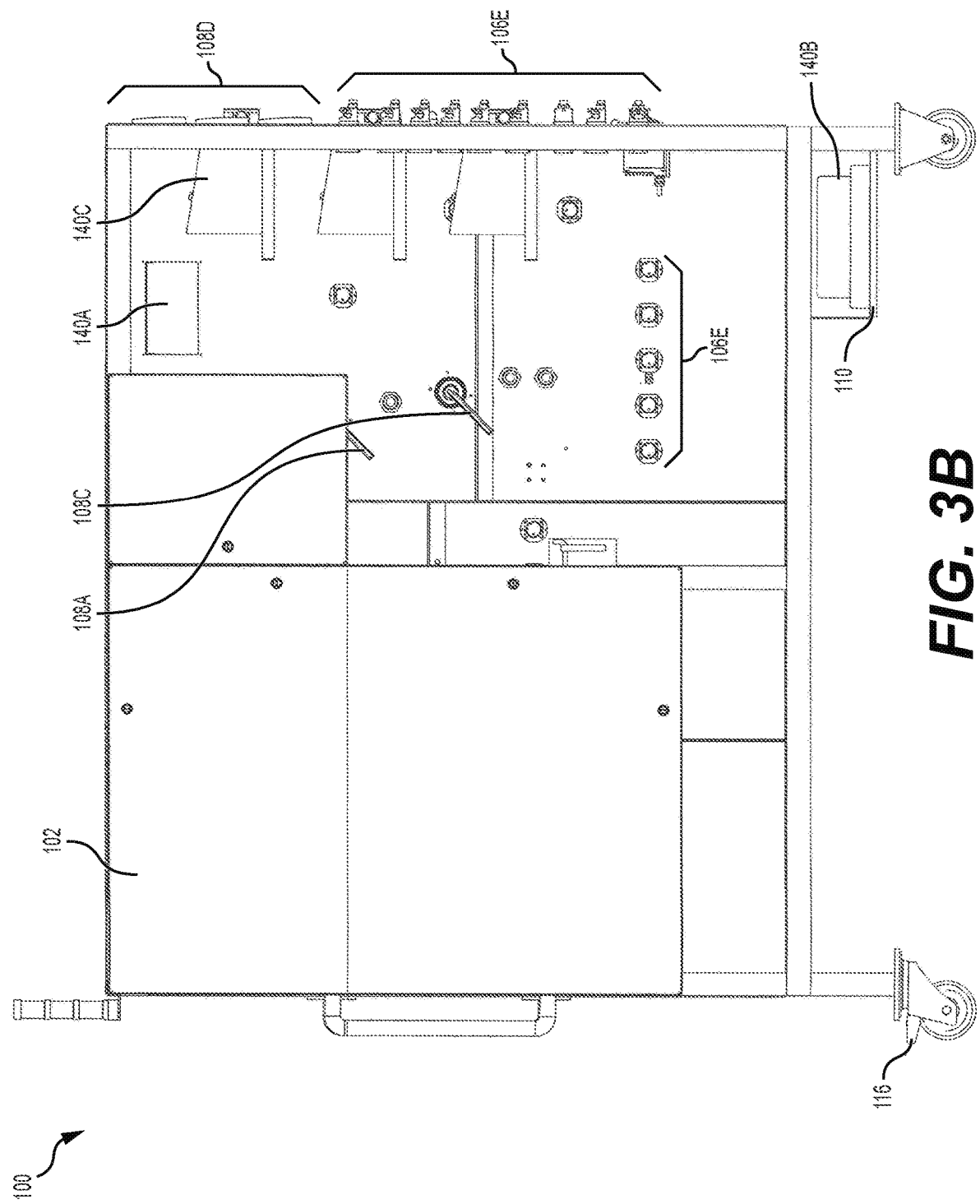
FIG. 3B is a back view of the example universal skid of FIG. 3A.

FIG. 3A is a perspective view of an example universal skid 100. FIG. 3B is a back view of the example universal skid 100 of FIG. 3A. FIG. 3C is a left view of the example universal skid 100 of FIG. 3A. FIG. 3D is a right view of the example universal skid 100 of FIG. 3A. The universal skid 100 can include a support 102, pumps 104, valves 106, sensors 108, a surge vessel support 110 (as illustrated in FIG. 3B), analyzer indicator transmitters 140A, and a scale 140B (as illustrated in FIG. 3B). As illustrated in FIG. 3B, the surge vessel support 110 can support a surge vessel 120 of a single-use kit 130. The scale 140B can measure a weight of a surge vessel 120. In some embodiments (not illustrated), the universal skid 100 can include a timer to measure mean residence time of a surge vessel 120 and/or flow channels.

The support 102 can be a moveable cart having rollers 116. The universal skid 100 can be a single solid and rigid structure. For example, all of the hardware components of the universal skid 100 can be mounted on the support 102. In some embodiments, all or some of hardware components of the universal skid 100 can be permanently mounted on the support 102. In some embodiments, some hardware components can be removable from the support 102. Examples of hardware components of a universal skid are described with respect to FIG. 1.

The pumps 104 can include diaphragm pumps 104C and centrifugal pumps 104D. A diaphragm pump 104 can be a positive displacement pump that uses a combination of a reciprocating action of a rubber, thermoplastic or Teflon diaphragm and suitable valves on either side of the diaphragm (check valve, butterfly valves, flap valves, or any other form of shut-off valves) to pump a fluid. A centrifugal pump 104D can be a mechanical device designed to move a fluid by means of transfer of rotational energy from one or more driven rotors.

The valves 106 can include control valves 106E and pressure control valves 106F. A control valve 106E can control a flow of fluid, such as an on-off type control valve. A pressure control valve 106F can control a pressure of fluid.

The sensors 108 can include sensors 108A-108C that measure a power or intensity of ultraviolet (UV) radiation, pH values, and conductivity in a liquid (e.g., buffer) and/or a liquid mixture (e.g., a biological sample, a processed biological sample, waste or the like), pressure sensors 108D that monitor a pressure of a liquid and/or a liquid mixture, flow sensors that measure a flow rate of a liquid and/or a liquid mixture, and other suitable sensors to detect data/ signals associated with the universal skid 100. As illustrated in FIG. 3A, sensors 108A and 108B can be used to measure UV, pH, and/or conductivity for flow-channel hardware sets 310 (as illustrated in FIG. 3B). Sensor(s) 108C can be used to measure UV, pH, and/or conductivity for a feed line.

Analyzer indicator transmitters 140A can receive and analyze data from sensors 108 and/or other hardware components.

Figure 3E:
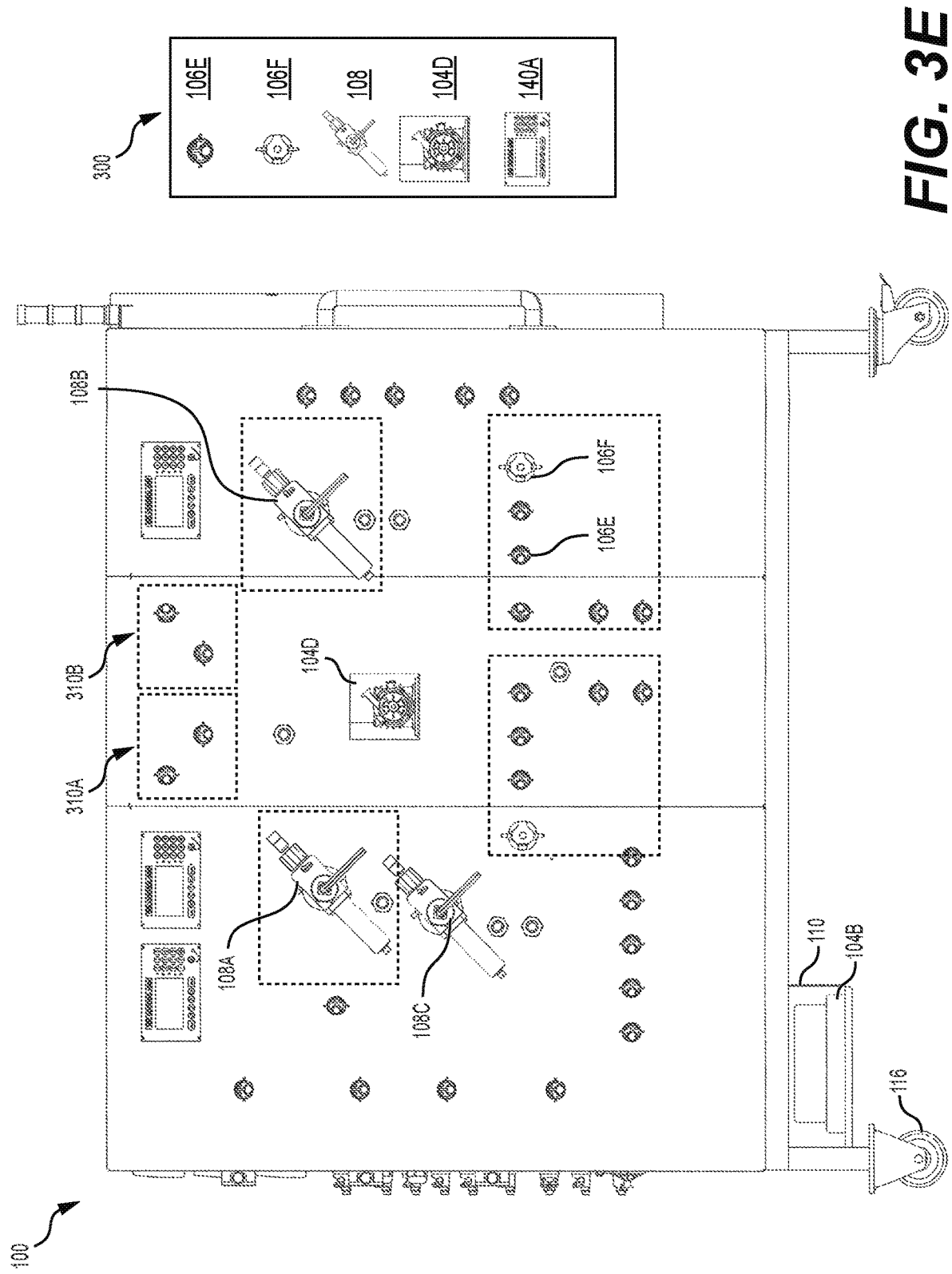
FIG. 3E is a front view of the example universal skid of FIG. 3A.

FIG. 3E is a front view of the example universal skid 100 of FIG. 3A. A legend 300 is given to depict symbols illustrated in FIGS. 3A-3E. As illustrated in FIG. 3E, the universal skid 100 can include two flow-channel hardware sets 310A (in a dotted line area) and 310B (in a dashed line area) for continuous processing. As illustrated, each of the flow-channel hardware sets 310 can include the same hardware components. For example, each of the flow-channel hardware sets 310 can include a plurality of valves 106 (e.g., control valves 106E and a pressure control valve 106F), and a sensor 108. The control valves 106E can control fluid flows entering and/or exiting one or more components of a respective flow channel coupled (e.g., inserted, connected, mounted, or assembled) to each of the flow-channel hardware sets 310. The pressure control valve 106F can control a pressure of fluid flows in the respective flow channel. The sensor 108 can monitor ultraviolet (UV), pH, and/or conductivity of a respective flow channel.

In some embodiments, each of the flow-channel hardware sets 310 can include more or fewer hardware components than those as illustrated in FIG. 3E. For example, each of the flow-channel hardware sets 310 can further include an analyzer indicator transmitter 140A and/or other suitable hardware components (e.g., valves, regulators, pumps, sensors, and the like). In some embodiments (not illustrated), each of the flow-channel hardware sets 310 can have different hardware components. For example, the flow-channel hardware set 310A can have more or fewer hardware components (e.g., support hardware components and/or valves) than the flow-channel hardware set 310B. In some embodiments, all of hardware components of a flow-channel hardware set 310 can be coupled (e.g., inserted, connected, mounted, or assembled) to a flow channel. In some embodiments, partial hardware components of a flow-channel hardware set 310 can be coupled to a flow channel. For example, some unit operations (e.g., VF, UF/DF, VI) may not use columns. The hardware components of the flow-channel hardware sets 310 for connecting to columns may not be used. In some embodiments (not illustrated), the universal skid 100 can include more than two flow-channel hardware sets 310 to support more than two flow channels.

Figure 4A:
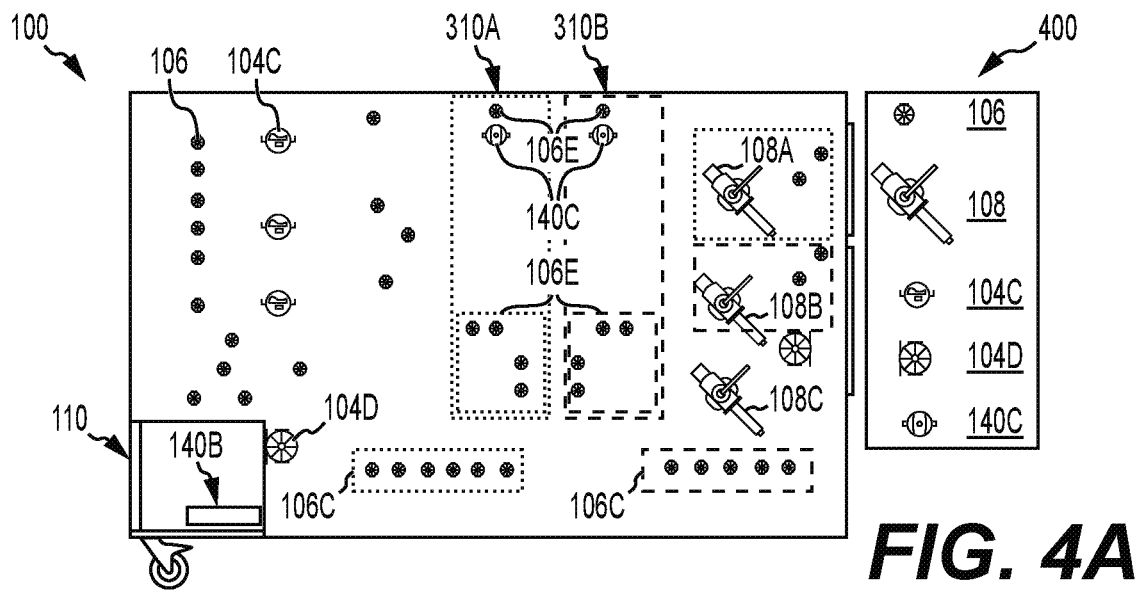
FIG. 4A is a front view of another example universal skid in accordance with some embodiments.
Figure 4B:
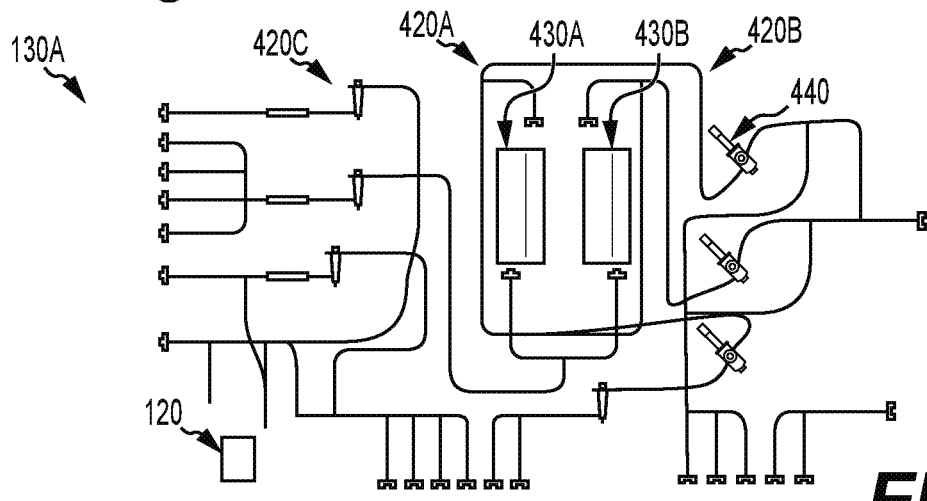
FIG. 4B illustrates an example single-use kit for chromatography.
Figure 4C:
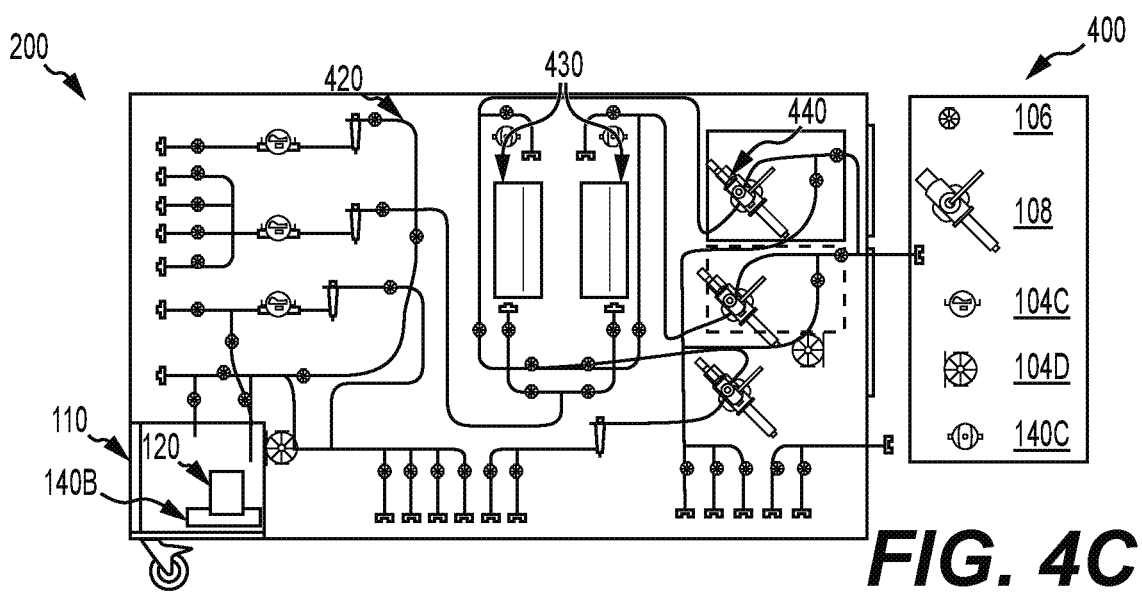
FIG. 4C is a front view of an example modular assembly having the example universal skid of FIG. 4A coupled with the example single-use kit of FIG. 4B.

The flow-channel hardware sets 310 allow continuous processing. In some embodiments, the flow-channel hardware sets 310 can allow flow channels to operate in parallel or in series to perform continuous processing over one or more unit operations. For example, a first flow-channel hardware set 310A can be coupled to a first flow channel that includes flow path elements and other suitable disposable and/or consumable components associated with a unit operation. The first flow channel can be a first portion of a single-use kit for a unit operation, the first portion coupled to the first flow-channel hardware 310A. For example, as illustrated in FIGS. 4A-4C, a first flow channel can have flow path elements 420A and a column 430A, the flow path elements 420A connecting to the column 430A. A second flow-channel hardware set 310A can be coupled to a second flow channel. In some embodiments, the second flow channel can be a second portion of the single-use kit for the same unit operation. For example, as illustrated in FIGS. 4A-4C, a second flow channel can have flow path elements 420B and a column 430B, the flow path elements 420B connecting to the column 430B. The first flow channel can be used for a first position for a processing step for a specific unit operation (e.g., one of Chrom, VF, UF/DF, VI, and other suitable unit operations). The second flow channel can be used for a second positon for the same processing step that is operated in the first flow channel. The second position can be different than the first position. A first position may refer to a location where a first flow-channel hardware 310A is located or where a first flow channel is located. A second position may refer to a location where a second flow-channel hardware 310B is located or where a second flow channel is located. The flow-channel hardware sets 310 can allow the first and second flow channels to operate in parallel such that fluid continuously flows into either the first flow channel or the second flow channel for the specific unit operation.

In some embodiments, the flow-channel hardware sets 310 can allow the first and second flow channels to operate in series such that fluid continuously flows into the first and second flow channels for the specific unit operation. For example, a output from the first flow channel can be an input to the second flow channel. The second flow channel can be used for a subsequent processing step (e.g., a different processing step that the processing step operated in the first flow channel) for the specific unit operation.

In such a way, the universal skid 100 can allow continuous processing between an inlet and an outlet of a single universal skid and/or between an inlet and an outlet of a single-use kit for a single unit operation.

Additionally, the flow-channel hardware sets 310 can allow flow channels to operate in parallel or in series to perform continuous processing over multiple unit operations. For example, a first flow-channel hardware set 310A can be coupled to a first flow channel that can be used for processing steps for a first unit operation (e.g., one of Chrom, VF, UF/DF, VI, and other suitable unit operations). For example, the first flow channel can be a portion of a first single-use kit for the first unit operation. A second flow-channel hardware set 310B can be coupled to a second flow channel that can be used for processing steps for a second unit operation (e.g., one of Chrom, VF, UF/DF, VI, and other suitable unit operations). For example, the second flow channel can be a portion of a second single-use kit for a second unit operation (e.g., one of Chrom, VF, UF/DF, VI, and other suitable unit operations). In some embodiments, the first unit operation can be the same as or different than the second unit operation. The flow-channel hardware sets 310 can allow the first and second flow channels to operate in parallel such that fluid continuously flows into either the first flow channel or second flow channel. In such a way, instead of batch processing, the parallel configuration of the flow channels provides the benefit of continuous processing.

In some embodiments, the flow-channel hardware sets 310 can allow the first and second flow channels to operate in series such that fluid continuously flows into the first flow channel for the first unit operation and the second flow channel for the second unit operation. For example, an output from the first flow channel for the first unit operation can be an input to the second flow channel for the second unit operation. Connecting the flow channels in series allows performing at least two unit operations on the same universal skid, thereby minimizing the number of universal skids used. Connecting multiple universal skids in series offers the ability for fully continuous processing (connecting all of multiple unit operations). In such a way, the series configurations of flow channels and/or multiple universal skids offer the ability for fully continuous processing (connecting all of multiple unit operations) and/or end-to-end continuous processing across multiple unit operations. Thus, universal skid(s) 100 can allow flow channels to be used both in the parallel configuration as taught herein for continuous processing and series configurations as taught herein for fully continuous processing.

In some embodiments, a single universal skid 100 can be used for a single unit operation and/or multiple unit operations. For example, as described above, the flow-channel hardware sets 310 can be used for a specific unit operation or multiple unit operations. A single-use kit(s) for a specific unit operation or multiple unit operations can be entirely or partially coupled to a single universal skid 100.

In some embodiments, the flow-channel hardware sets 310 can allow flow channels to operate in parallel, to be switchable, and/or to be replaceable. For example, if the flow-channel hardware set 310A is occupied (e.g., for processing biological samples or for buffer flow), the flow-channel hardware set 310B can support a flow channel to perform the same processing step in parallel (e.g., for the same unit operation) or perform a different processing step in parallel (e.g., for a different unit operation), and vice versa. If the flow-channel hardware set 310A fails to operate, the flow-channel hardware set 310B can be used for processing, and vice versa. If a flow channel coupled to the flow-channel hardware set 310A fails to operate, another flow channel can replace the failed flow channel by coupling to the flow channel hardware set 310B, and vice versa.

In some embodiments, at least by allowing continuous processing for a specific unit operation and/or multiple unit operations as described above, the universal skid 100 can cause zero, reduced, or optimized (e.g., minimal) hold-up volume for a specific unit operation and/or multiple unit operations, zero, reduced, or optimized (e.g., minimal) mean residence time in a surge vessel 120 and/or each flow channel, and/or zero, reduced, or optimized (e.g., minimal) volume of the surge vessel 120 and/or each flow channel. For example, mean residence time of the surge vessel 120 and/or each flow channel can be less than about 30 minutes (e.g., about 10 minutes to about 30 minutes). In another example, mean residence time of the surge vessel 120 and/or each flow channel can be less than about 60 minutes (e.g., about 40 minutes to about 60 minutes). In some embodiments, mean residence time of the surge vessel 120 and/or each flow channel can be less than about 120 minutes. The shortened or limited mean residence time can cause a reduction in the hold-up volume and volume of the surge vessel 120. Further, at least because of reduction in mean residence time, the universal skid 100 can allow the surge vessel 120 to receive and send flow at the same time, and/or allow more flexible use of the surge vessel 120 (e.g., allowing use of different quantities, different sizes, different arrangements, or different volumes of surge vessels).

FIG. 4A is a front view of another example universal skid 100. A legend 400 is given to depict symbols illustrated in FIG. 4A. The universal skid 100 can include valves 106, sensors 108 (e.g., two UV, pH, conductivity sensors 108A and 108B for flow-channel hardware sets 310, and one UV, pH, conductivity sensor 108C for a feed line), pumps 104 (e.g., diaphragm pump 104C and centrifugal pump 104D) and regulators 140C (e.g., back pressure regulators), a surge vessel support 110, and a scale 140B. Each of the flow-channel hardware sets 310 can include a plurality of valves 106, a regulator 140C, and a sensor 108. The valves 160C can control fluid flows entering a respective flow channel. The valves 160E can control fluid flows entering and/or exiting a respective column 430. The regulator 140C can regulate a fluid flow passing through a respective column 430. The sensor 108A, 108B can monitor ultraviolet (UV), pH, and/or conductivity of a respective flow channel. In some embodiments, the flow-channel hardware set 310A (in a dotted line area) can have more or fewer hardware components (e.g., support hardware components and/or valves)

than the flow-channel hardware set 310B (in a dashed line area). In some embodiments, all of hardware components of the flow-channel hardware set 310B can be coupled (e.g., inserted, connected, mounted, or assembled) to a flow channel. In some embodiments, partial hardware components of the flow-channel hardware set 310B can be coupled (e.g., inserted, connected, mounted, or assembled) to a flow channel. In some embodiments (not illustrated), the universal skid 100 can include more than two flow-channel hardware sets to support more than two flow channels.

FIG. 4B is a front view of an example single-use kit 130A for chromatography. The single-use kit 130A includes flow path elements 420 (e.g., tubing, fluid conduits, pipelines, or the like), columns 430, sensors 440, a surge vessel 120, and other suitable other suitable disposable and/or consumable components needed for performing chromatography.

FIG. 4C is a front view of an example modular assembly 200A having the example universal skid 100 of FIG. 4A coupled with the example single-use kit 130A of FIG. 4B. As illustrated in FIG. 4C, the flow path elements 420 are coupled (e.g., inserted, connected, mounted, or assembled) with various valves 106. The columns 430 are coupled with the universal skid 100 via mounting hardware (not shown) of the universal skid 100. The sensors 440 are coupled with the sensors 108. The surge vessel 120 is placed on the scale 140B. A first flow channel having flow path elements 420A connecting to the column 430A can be coupled with the flow-channel hardware set 310A. A second flow channel having flow path elements 420B connecting to the column 430B can be coupled with the flow-channel hardware set 310B.

As illustrated in FIGS. 4A-4C, the universal skid 100 allows flow channels to operate in parallel to perform continuous processing for chromatography. For example, a first flow-channel hardware set 310A can be coupled to a first flow channel (e.g., a flow channel having flow path elements 420A connecting to a columns 430A). A second flow-channel hardware set 310B can be coupled to a second flow channel (e.g., a flow channel having flow path elements 420B connecting to a columns 430B). The first flow channel can be used for a first position for a first processing step for chromatography. The second flow channel can be used for a second positon for the same processing step. The first position can be different than the second position. A first position may refer to a location where a first flow-channel hardware 310A is located or where a first flow channel is located. A second position may refer to a location where a second flow-channel hardware 310B is located or where a second flow channel is located. The flow-channel hardware sets 310 can allow the first and second flow channels to operate in parallel such that fluid continuously flows into either the first flow channel or the second flow channel for chromatography. In some embodiments (not illustrated), the flow-channel hardware sets 310 can allow the first and second flow channels to operate in series such that fluid continuously flows into the first and second flow channels for multi-column chromatography. For example, the first processing step can be different than the second processing step. An output of the first processing step can be an input of the second processing, and vice versa.

In such a way, instead of batch processing, at by allowing flow channels to be used both in parallel configuration and in-series configuration, the universal skid 100 can and allow continuous processing for chromatography between an inlet and an outlet of the universal skid 100 and/or between an inlet and an outlet of the single-use kit 130 for chromatography. Additionally, the universal skid 100 can cause zero, reduced, or an optimized (e.g., minimal) hold-up volume for chromatography, zero, reduced, or optimized (e.g., minimal) mean residence time in the surge vessel 120 and/or flow channels, and/or zero, reduced, or optimized (e.g., minimal) volume of the surge vessel 120 and/or flow channels. For example, mean residence time of the surge vessel 120 and/or flow channels can be less than about 30 minutes (e.g., about 10 minutes to about 30 minutes). In another example, mean residence time of the surge vessel 120 and/or flow channels can be less than about 60 minutes (e.g., about 40 minutes to about 60 minutes). In some embodiments, mean residence time of the surge vessel 120 and/or flow channels can be less than about 120 minutes. The shortened or limited mean residence time can cause a reduction in the hold-up volume and volume of the surge vessel 120 and/or flow channels. Further, at least because of reduction in mean residence time, the universal skid 100 can allow the surge vessel 120 to receive and send flow at the same time, and/or allow more flexible the surge vessel 120 (e.g., allowing use of different quantities, different sizes, different arrangements, or different volumes of surge vessels).

Figure 5B:
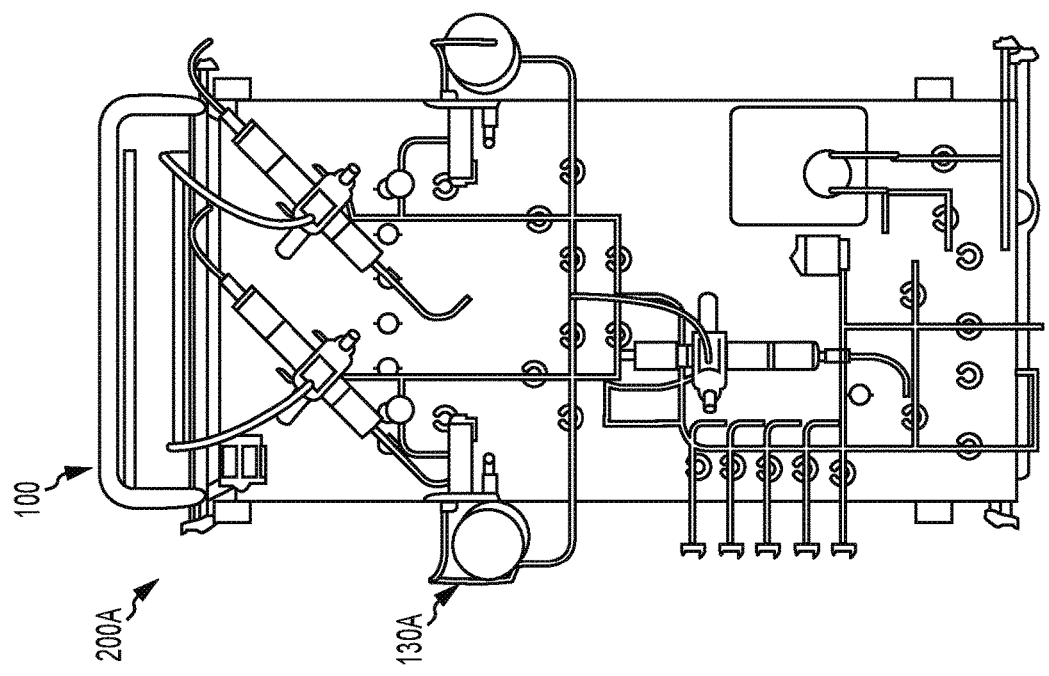
FIG. 5B is a top view of the example modular assembly of FIG. 5A.
Figure 5A:
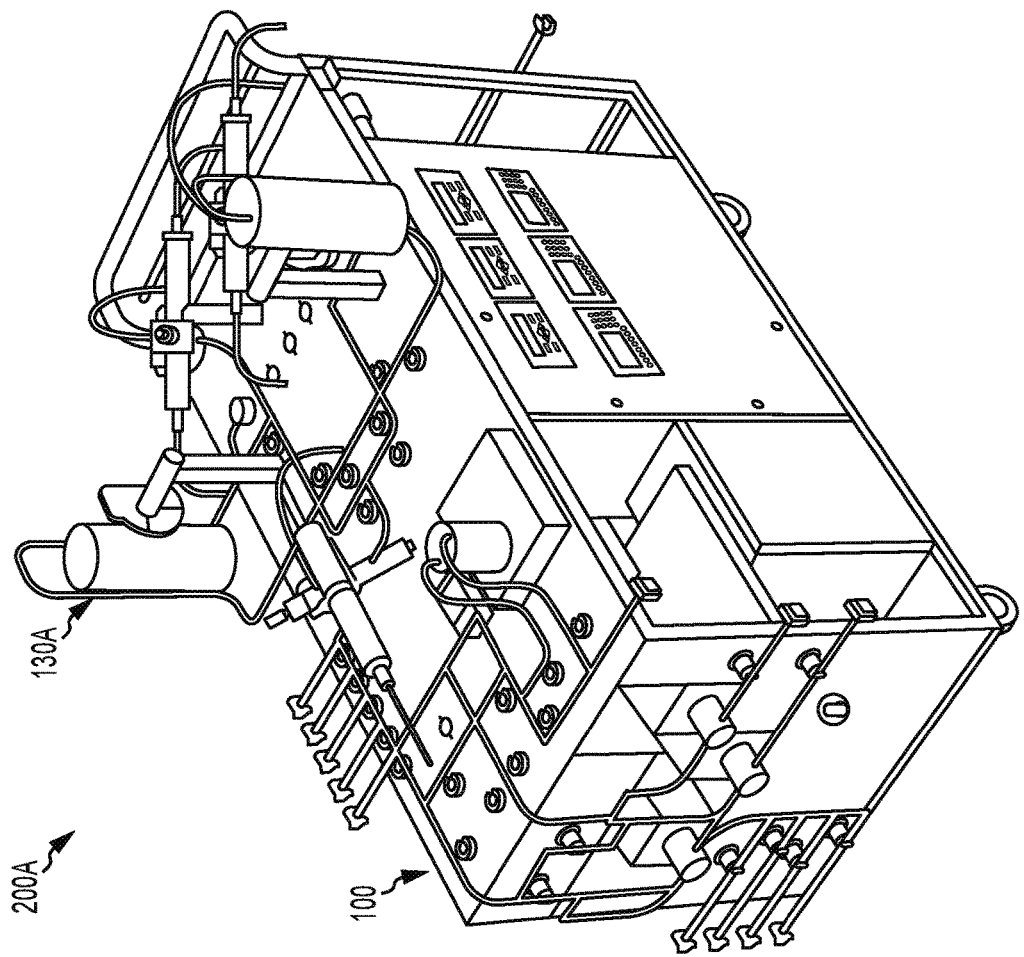
FIG. 5A is a perspective view of an example modular assembly for chromatography in accordance with some embodiments.
Figure 5C:
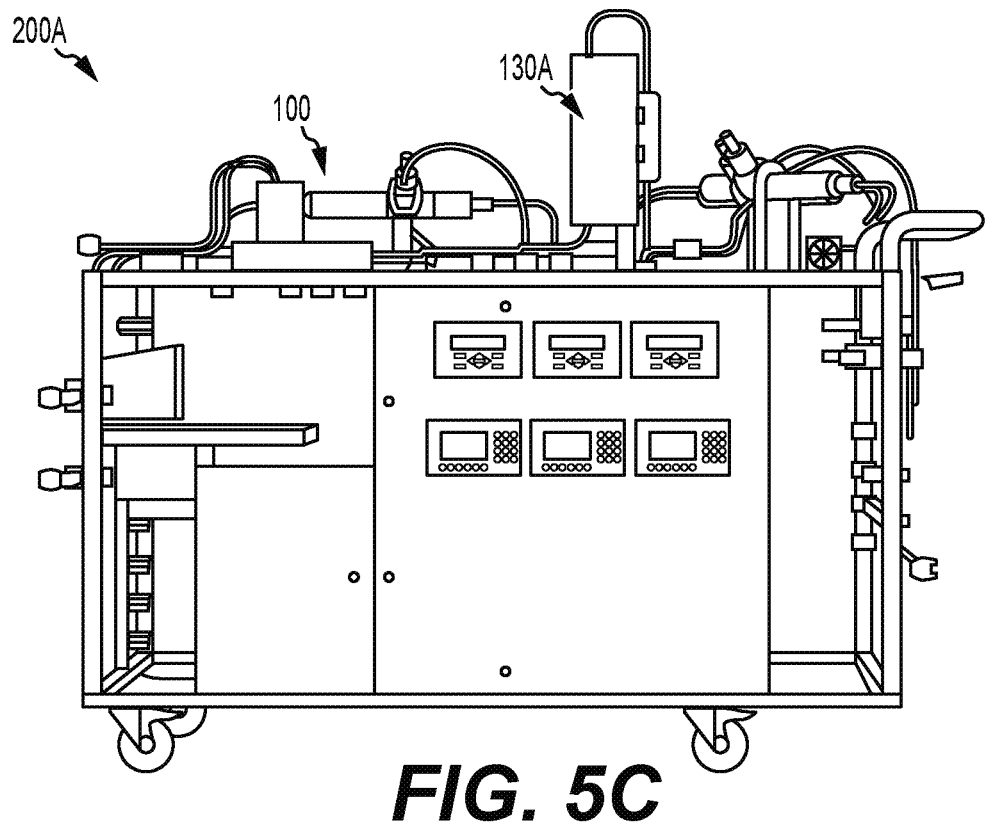
FIG. 5C is a front-side view of the example modular assembly of FIG. 5A.
Figure 5D:
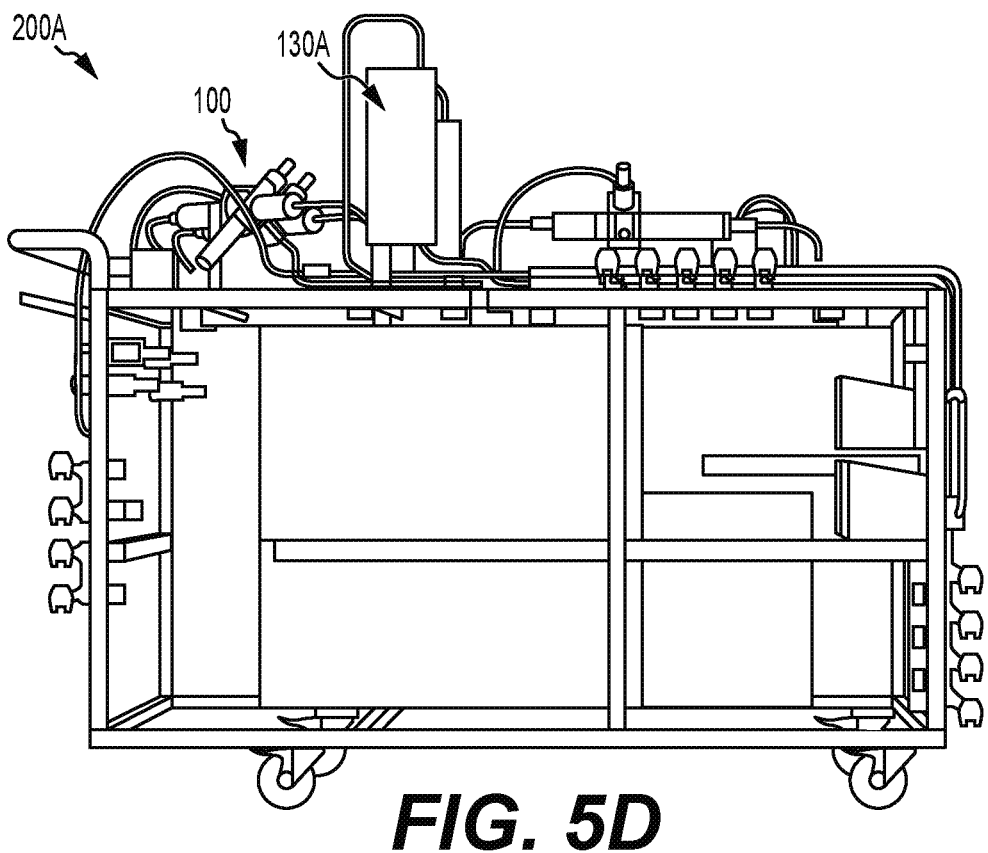
FIG. 5D is a back-side view of the example modular assembly of FIG. 5A.
Figure 5F:
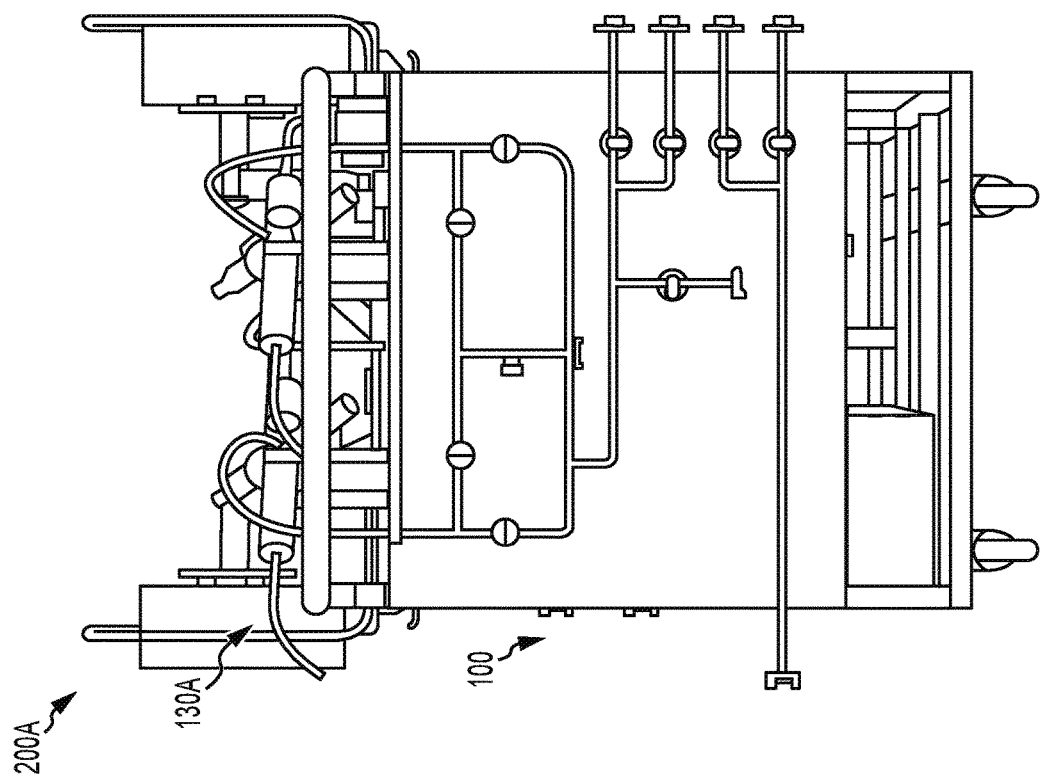
FIG. 5F is a left-side view of the example modular assembly of FIG. 5A.
Figure 5E:
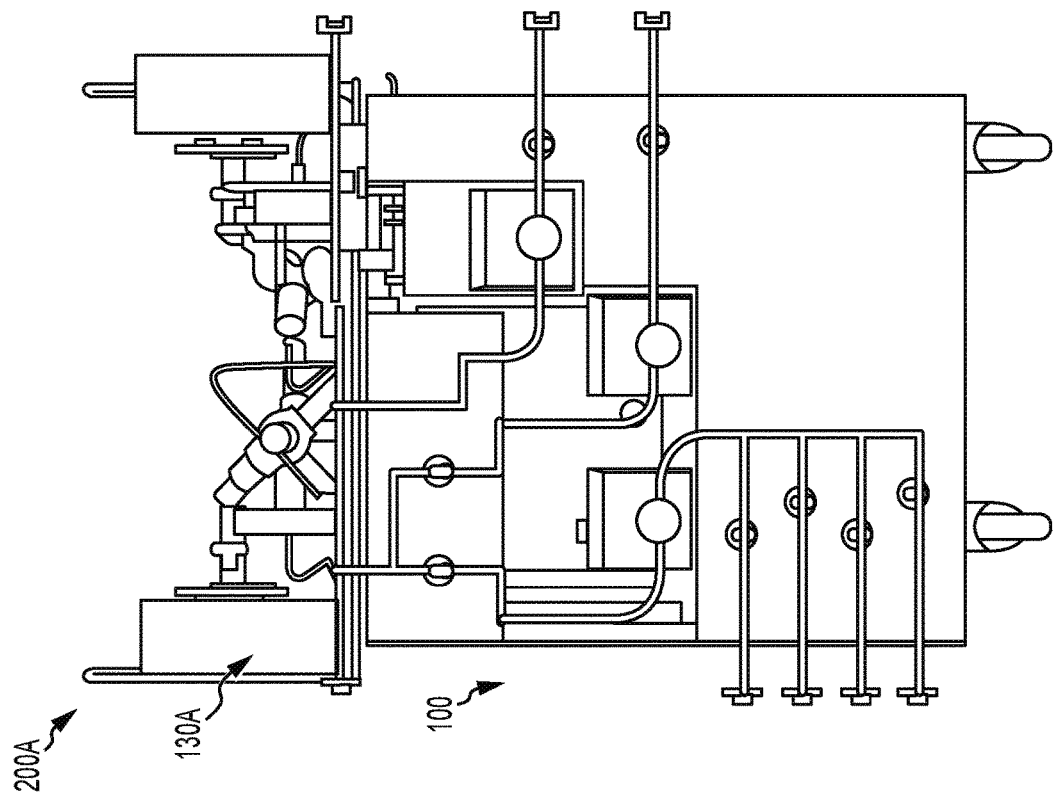
FIG. 5E is a right-side view of the example modular assembly of FIG. 5A.

FIG. 5A is a perspective view of an example modular assembly 200A for chromatography. FIG. 5B is a top view of the example modular assembly 200A of FIG. 5A. FIG. 5C is a front-side view of the example modular assembly 200A of FIG. 5A. FIG. 5D is a back-side view of the example modular assembly 200A of FIG. 5A. FIG. 5E is a right-side view of the example modular assembly 200A of FIG. 5A. FIG. 5F is a left-side view of the example modular assembly 200A of FIG. 5A. For illustration purposes, the modular assembly 200A can be a universal skid 100 coupled (e.g., inserted, connected, mounted, or assembled) with a single-use kit 130A for chromatography. It should be understood that a modular assembly 200 can perform any other suitable unit operations if a universal skid 100 is coupled with any other single-use kits 130 for that suitable unit operations (e.g., one or more kits for Chrom, VI, VF, UF/DF, or any other suitable unit operations). Examples are described with respect to FIGS. 6A-6D.

Although various example embodiments described herein have certain configurations (e.g., quantities, locations) of hardware components, one of ordinary skill of the art in view of the present disclosure will appreciate that a universal skid may have different configurations than the universal skid 100 as illustrated in FIGS. 3-5. Further, one of ordinary skill of the art in view of the present disclosure will appreciate that hardware components of flow-channel hardware sets for continuous processing can be different than flow-channel hardware sets 310 illustrated in FIGS. 3 and 4. One of ordinary skill of the art in view of the present disclosure will also appreciate that a universal skid can have more than two flow-channel hardware sets for continuous processing and hardware components of each of flow-channel hardware set can be different. One of ordinary skill of the art in view of the present disclosure will also appreciate that a universal skid may have additional hardware components not explicitly described herein in some embodiments.

Figure 6A:
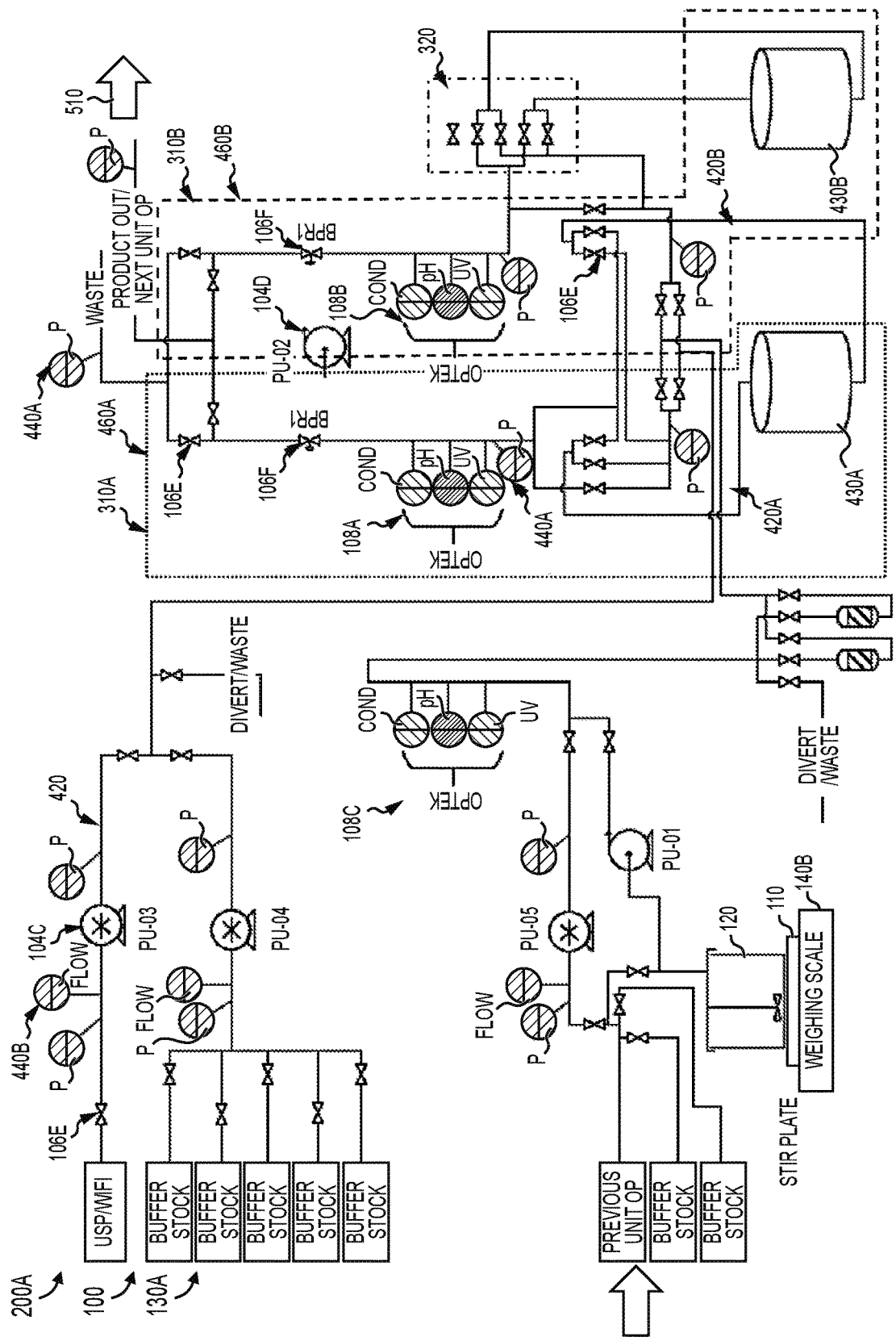
FIG. 6A is a piping and instrumentation diagram (P&ID) illustrating a modular assembly for chromatography in accordance with some embodiments.

FIG. 6A is a piping and instrumentation diagram (P&ID) illustrating a modular assembly 200A for chromatography. The modular assembly 200A can be a universal skid 100 as illustrated in FIGS. 3A-3E coupled (e.g., assembled, connected, mounted, or inserted) with a single-use kit 130A for chromatography. Hardware components of the universal skid 100 and the single-use kit 130A can be represented using standard notations/symbols of P&ID software. For illustration and simplicity purposes, one of the same hardware components is labeled and other same hardware components are not labeled. As illustrated, the universal skid 100 can include pumps 104C, 104D, valves 106E, 106F, sensors 108A-108C, a surge vessel support 110 and a scale 140B. The single-use kit 130A can include flow path elements 420 (e.g., tubing, fluid conduits, pipelines, or the like), columns 430, pressure sensors 440A, flow sensors 440B, a surge vessel 120, and other suitable disposable and/or consumable components (not illustrated) needed for performing chromatography. A dotted line area can include a first flow-channel hardware set 310A coupled (e.g., assembled, inserted, connected, or mounted) with a first flow channel 460A. The first flow-channel hardware set 310A can include valves 106E, 106F, and a sensor 108A. The first flow channel 460A can include flow path elements 420A, pressure sensors 440A and a column 430A. A dashed line area can include a second flow-channel hardware set 310B coupled (e.g., assembled, inserted, connected, or mounted) with a second flow channel 460B. The second flow-channel hardware set 310B can include valves 106E, 106F, and a sensor 108B. The second flow channel 460B can include flow path elements 420B, pressure sensors 440A and a column 430B. In some embodiments, the second flow-channel hardware set 310B can further include valves 106E in a dashed dotted line area 320. The second flow channel 460B can further include flow path elements 420B connecting to the valves 106E in the dashed dotted line area 320 and the column 430B.

The first flow channel 460A can be used for a first position for a processing step for chromatography to process a biological sample received from a previous unit operation 500 (e.g., a same unit operation for Chrom or a different unit operation for VI, VF, UF/DF, or the like). The second flow channel 460B can be used for a second position for the same processing step that is operated in the first flow channel 460B. The first position can be different than the second position. A first position may refer to a location where a first flow-channel hardware 310A is located or where a first flow channel is located. A second position may refer to a location where a second flow-channel hardware 310B is located or where a second flow channel is located. The flow-channel hardware sets 310 can allow the first and second flow channels 460A, 460B to operate in parallel such that fluid continuously flows into either the first flow channel 460A or the second flow channel 460B for chromatography. In some embodiments (not illustrated), the flow-channel hardware sets 310 can allow the first and second flow channels 460 to operate in series such that fluid continuously flows into the first and second flow channels 460 for multi-column chromatography. For example, an output from the first flow channel 460A can be an input to the second flow channel 460B. The second flow channel 460B can be used for a subsequent processing step (e.g., a different processing step) for multi-column chromatography.

As illustrated in FIG. 6A, a combined output from the first flow channel 460A and the second flow channel 460B can be a biological product or an input to a next unit operation 510 (e.g., a same unit operation for Chrom or a different unit operation for VI, VF, UF/DF, or the like). At least by allowing flow channels to be arranged in an in-parallel configuration or an in-series configuration, the flow-channel hardware sets 310 can allow continuous processing between an inlet and an outlet of the universal skid 100 and/or between an inlet and an outlet of the single-use kit 130A for chromatography. Additionally, at least by continuous processing as taught herein, the universal skid 100 can cause zero, limited or optimized (e.g., minimal) hold-up volume for chromatography, zero, reduced, or optimized (e.g., minimal) mean residence time in the surge vessel 120 and/or flow channels 460, and/or zero, reduced, or optimized (e.g., minimal) volume of the surge vessel 120 and/or flow channels 460. For example, mean residence time of the surge vessel 120 and/or flow channels 460 can be less than about 30 minutes (e.g., about 10 minutes to about 30 minutes). In another example, mean residence time of the surge vessel 120 and/or flow channels 460 can be less than about 60 minutes (e.g., about 40 minutes to about 60 minutes). In some embodiments, mean residence time of the surge vessel 120 and/or flow channels 460 can be less than about 120 minutes. The shortened or limited mean residence time can cause a reduction in the hold-up volume and volume of the surge vessel 120 and/or flow channels 460. Further, at least because of reduction in mean residence time, the universal skid 100 can allow the surge vessel 120 to receive and send flow at the same time, and/or allow more flexible us of the surge vessel 120 (e.g., allowing use of different quantities, different sizes, different arrangements, or different volumes of surge vessels).

Figure 6B:
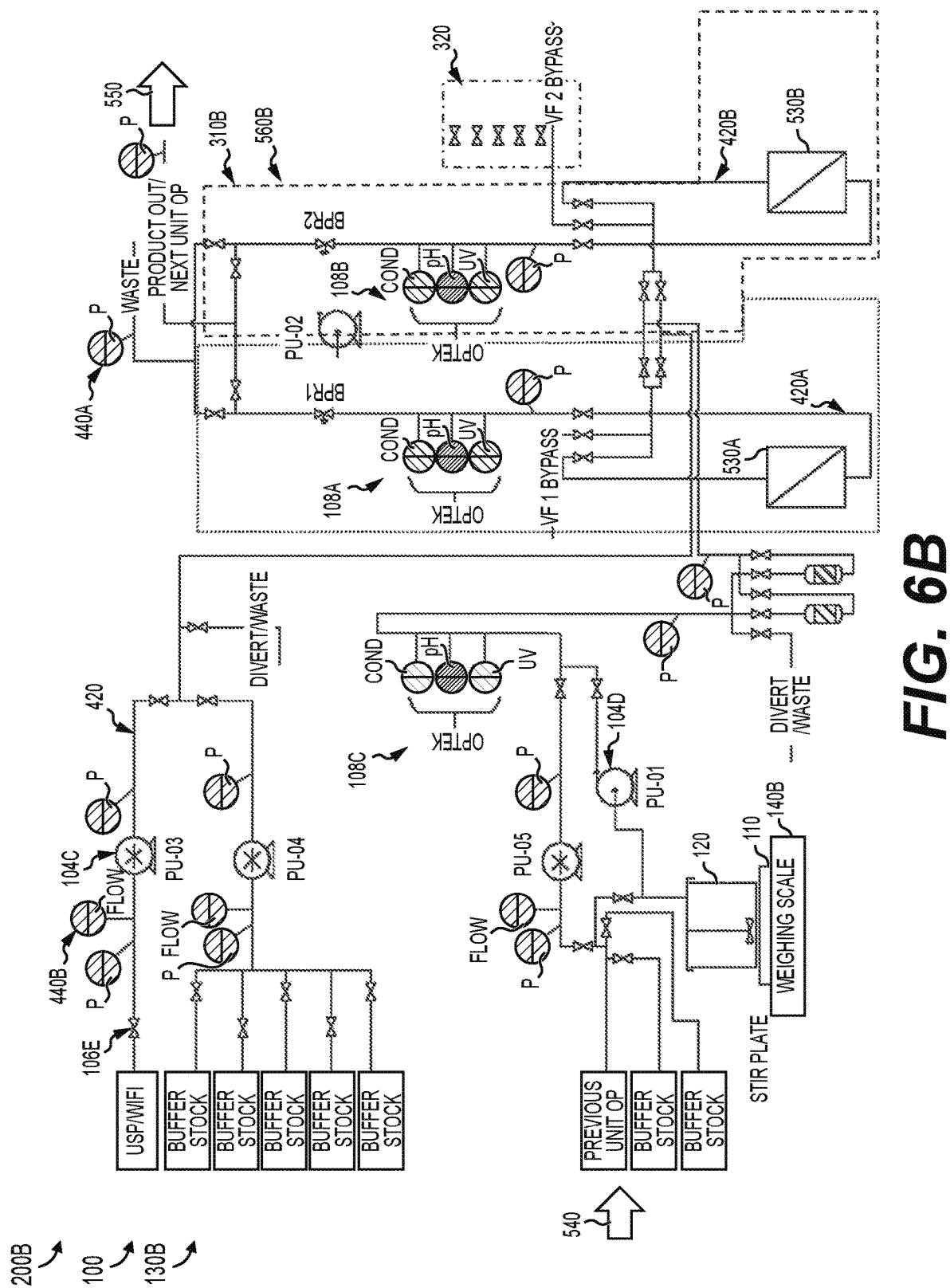
FIG. 6B is a P&ID illustrating a modular assembly for viral filtration in accordance with some embodiments.

FIG. 6B is a P&ID illustrating a modular assembly 200B for VF. The modular assembly 200B can be a universal skid 100 as illustrated in FIG. 6A coupled (e.g., assembled, connected, mounted, or inserted) with a single-use kit 130B for VF. Hardware components of the universal skid 100 and the single-use kit 130B can be represented using standard notations/symbols of P&ID software. For illustration and simplicity purpose, one of the same hardware components is labeled and other same hardware components are not labeled. As illustrated, the single-use kit 130B can include flow path elements 420 (e.g., tubing, fluid conduits, pipelines, or the like), VF filters 530, pressure sensors 440A, flow sensors 440B, a surge vessel 120, and other suitable disposable and/or consumable components (not illustrated) needed for performing VF. A dotted line area can include a first flow-channel hardware set 310A coupled (e.g., assembled, inserted, connected, or mounted) with a first flow channel 560A. The first flow-channel hardware set 310A can include valves 106E, 106F, and a sensor 108A. The first flow channel 560A can include flow path elements 420A, pressure sensors 440A and a VF filter 530A. A dashed line area can include a second flow-channel hardware set 310B coupled (e.g., assembled, inserted, connected, or mounted) with a second flow channel 460B. The second flow-channel hardware set 310B can include valves 106E, 106F, and a sensor 108B. The second flow channel 560B can include flow path elements 420B, pressure sensors 440A and a VF filter 530B. In some embodiments, the second flow-channel hardware set 310B can further include valves 106E in a dashed dotted line area 320, which are not used for VF.

The first flow channel 560A can be used for a processing step for VF to process a biological sample received from a previous unit operation 540 (e.g., a same unit operation for VF or a different unit operation for VI, Chrom, UF/DF, or the like). The second flow channel 560B can be used for a second position for the same processing step that is operated in the first flow channel 560B. The first position can be different than the second position. A first position may refer to a location where a first flow-channel hardware 310A is located or where a first flow channel is located. A second position may refer to a location where a second flow-channel hardware 310B is located or where a second flow channel is located. The flow-channel hardware sets 310 can allow the first and second flow channels 560A, 560B to operate in parallel such that fluid continuously flows into either the first flow channel 560A or the second flow channel 560B for VF. In some embodiments (not illustrated), the flow-channel hardware sets 310 can allow the first and second flow channels 560 to operate in series such that fluid continuously flows into the first and second flow channels 560 for VF. For example, an output from the first flow channel 560A can be an input to the second flow channel 560B. The second flow channel 560B can be used for a subsequent processing step (e.g., a different processing step) for VF.

As illustrated in FIG. 6B, a combined output from the first flow channel 560A and the second flow channel 560B can be a biological product or an input to a next unit operation 550 (e.g., a same unit operation for VF or a different unit operation for VI, Chrom, UF/DF, or the like). In such a way, at least by allowing flow channels to be used in both an in-parallel configuration and an in-series configuration, the flow-channel hardware sets 310 can allow continuous processing between an inlet and an outlet of the universal skid 100 and/or between an inlet and an outlet of the single-use kit 130B for VF. Additionally, at least by continuous processing as taught herein, the universal skid 100 can cause zero, reduced, or and/or optimized (e.g., minimal) hold-up volume for VF, zero, reduced, or optimized (e.g., minimal) mean residence time in the surge vessel 120 and/or flow channels 560, and/or zero, reduced, or optimized (e.g., minimal) volume of the surge vessel 120 and/or flow channels 560. For example, mean residence time of the surge vessel 120 and/or flow channels 560 can be less than about 30 minutes (e.g., about 10 minutes to about 30 minutes). In another example, mean residence time of the surge vessel 120 and/or flow channels 560 can be less than about 60 minutes (e.g., about 40 minutes to about 60 minutes). In some embodiments, mean residence time of the surge vessel 120 and/or flow channels 560 can be less than about 120 minutes. The shortened or limited mean residence time can cause a reduction in the hold-up volume and volume of the surge vessel 120 and/or flow channels 560. Further, at least because of reduction in mean residence time, the universal skid 100 can allow the surge vessel 120 to receive and send flow at the same time, and/or allow more flexible use of the surge vessel 120 (e.g., allowing use of different quantities, different sizes, different arrangements, or different volumes of surge vessels).

Figure 6C:
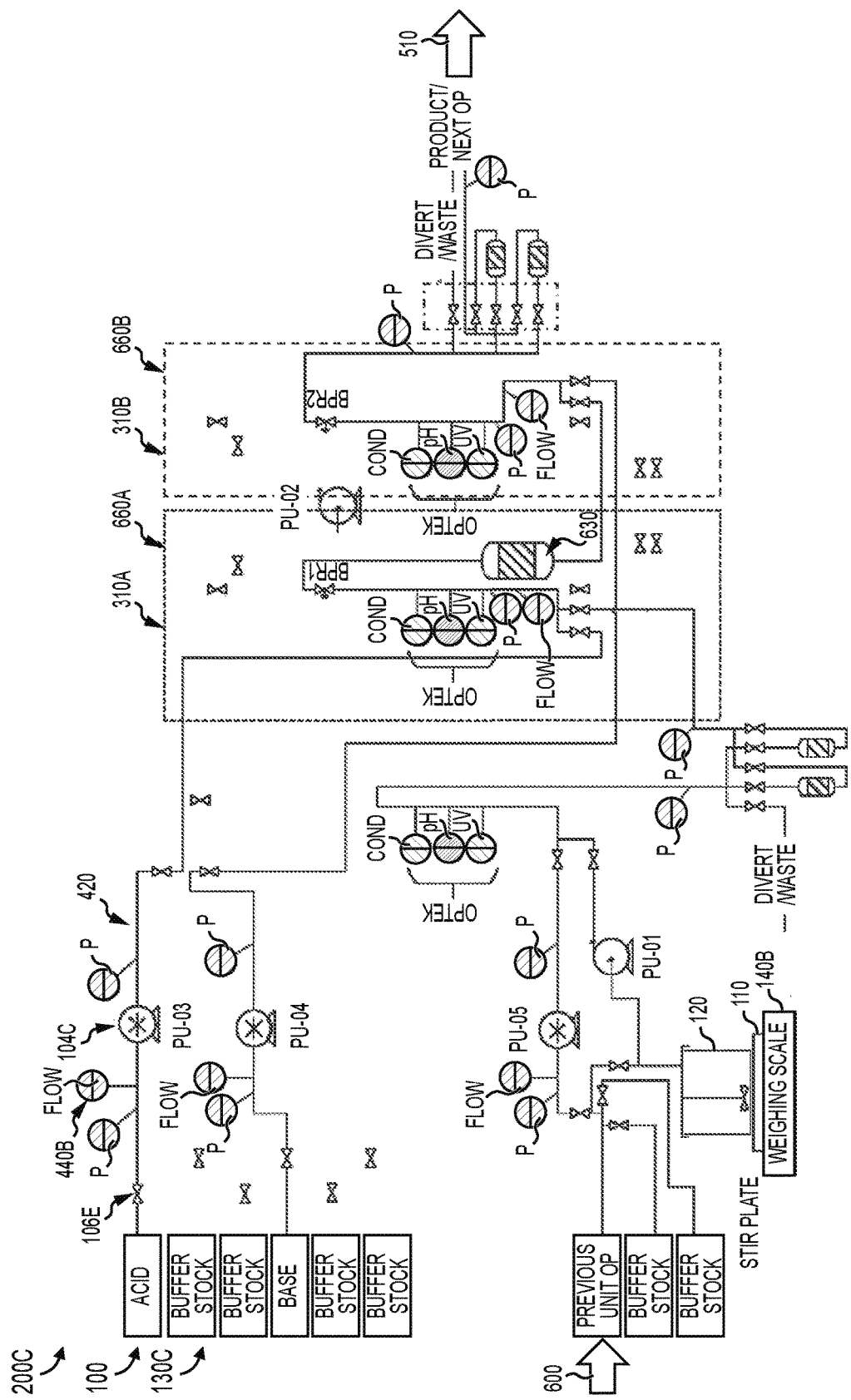
FIG. 6C is a P&ID illustrating a modular assembly for virus inactivation in accordance with some embodiments.

FIG. 6C is a P&ID illustrating a modular assembly 200C for VI. The modular assembly 200C can be a universal skid 100 as illustrated in FIG. 6A coupled (e.g., assembled, connected, mounted, or inserted) with a single-use kit 130C for VI. Hardware components of the universal skid 100 and the single-use kit 130C can be represented using standard notations/symbols of P&ID software. For illustration and simplicity purposes, one of the same hardware components is labeled and other same hardware components are not labeled. As illustrated, the single-use kit 130C can include flow path elements 420 (e.g., tubing, fluid conduits, pipelines, or the like), a container 630, pressure sensors 440A, flow sensors 440B, a surge vessel 120, and other suitable disposable and/or consumable components (not illustrated) needed for performing VI. A dotted line area can include a first flow-channel hardware set 310A coupled (e.g., assembled, inserted, connected, or mounted) with a first flow channel 660A. The first flow-channel hardware set 310A can include valves 106E, 106F, and a sensor 108A. The first flow channel 660A can include flow path elements 420A, pressure sensors 440A, flow sensors 440B, and a container 630. A dashed line area can include a second flow-channel hardware set 310B coupled (e.g., assembled, inserted, connected, or mounted) with a second flow channel 660B. The second flow-channel hardware set 310B can include valves 106E, 106F, and a sensor 108B. The second flow channel 660B can include flow path elements 420B, pressure sensors 440A, and flow sensors 440B. In some embodiments, the second flow-channel hardware set 310B can further include valves 106E in a dashed dotted line area 320. As illustrated, some valves 106E of the first and second flow-channel hardware sets 310 are not used for VI.

The first flow channel 660A can be used for a processing step for VI to process a biological sample received from a previous unit operation 600 (e.g., a same unit operation for VI or a different unit operation for VF, Chrom, UF/DF, or the like). An output from the first flow channel 660A can be an input to the second flow channel 660B. The second flow channel 660B can be used for a subsequent processing step (e.g., a different processing step) for VI. An output from the second flow channel 660B can be a biological product or an input to a next unit operation 610 (e.g., a same unit operation for VI or a different unit operation for VF, Chrom, UF/DF, or the like). In such a way, the flow-channel hardware sets 310 can allow the first and second flow channels 660 to operate in series such that fluid continuously flows into the first and second flow channels 660 for VI, thereby allowing continuous processing between an inlet and an outlet of the universal skid 100 and/or between an inlet and an outlet of the single-use kit 130C for VI. Additionally, at least by continuous processing as taught herein, the universal skid 100 can cause zero, reduced, or optimized (e.g., minimal) hold-up volume for VI, zero, reduced, or optimized (e.g., minimal) mean residence time in the surge vessel 120 and/or flow channels 660, and/or zero, reduced, or optimized (e.g., minimal) volume of the surge vessel 120 and/or flow channels 660. For example, mean residence time of the surge vessel 120 and/or flow channels can be less than about 30 minutes (e.g., about 10 minutes to about 30 minutes). In another example, mean residence time of the surge vessel 120 and/or flow channels can be less than about 60 minutes (e.g., about 40 minutes to about 60 minutes). In some embodiments, mean residence time of the surge vessel 120 and/or flow channels can be less than about 120 minutes. The shortened or limited mean residence time can cause a reduction in the hold-up volume and volume of the surge vessel 120 and/or flow channels. Further, at least because of reduction in mean residence time, the universal skid 100 can allow the surge vessel 120 to receive and send flow at the same time, and/or allow more flexible use of the surge vessel 120 (e.g., allowing use of different quantities, different sizes, different arrangements, or different volumes of surge vessels).

Figure 6D:
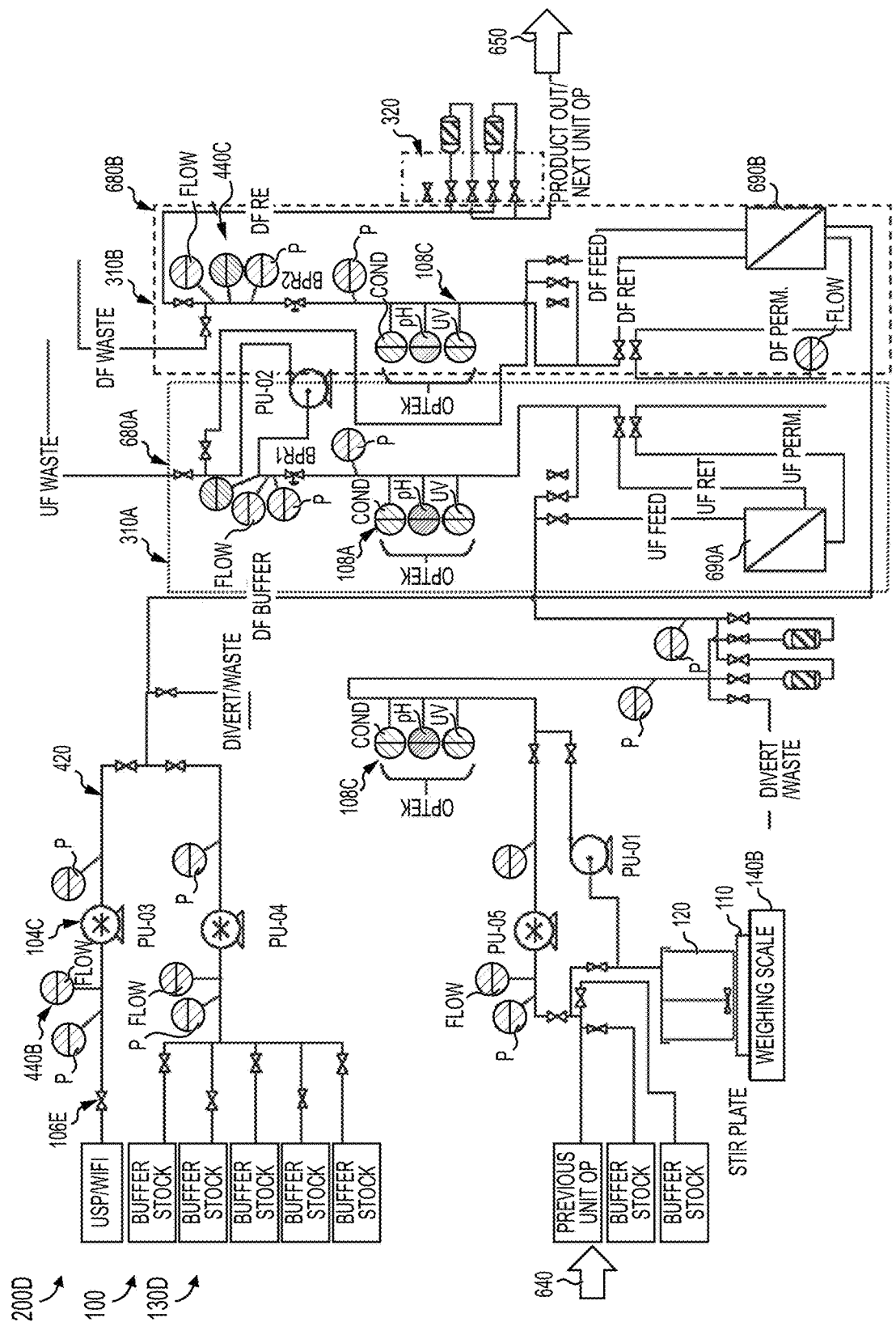
FIG. 6D is a P&ID illustrating a modular assembly for ultrafiltration/diafiltration in accordance with some embodiments.

FIG. 6D is a P&ID illustrating a modular assembly 200D for UF/DF. The modular assembly 200D can be a universal skid 100 as illustrated in FIG. 6A coupled (e.g., assembled, connected, mounted, or inserted) with a single-use kit 130D for UF/DF. Hardware components of the universal skid 100 and the single-use kit 130D can be represented using standard notations/symbols of P&ID software. For illustration and simplicity purposes, one of the same hardware components is labeled and other same hardware components are not labeled. As illustrated, the single-use kit 130D can include flow path elements 420 (e.g., tubing, fluid conduits, pipelines, or the like), UF/DF filters 690, pressure sensors 440A, flow sensors 440B, diavolume sensors 440C, a surge vessel 120, and other suitable disposable and/or consumable components (not illustrated) needed for performing UF/DF. A diavolume sensor 440C can measure a diavolume that refers to a total buffer volume introduced to an operation during diafiltration divided by an initial retentate volume. A dotted line area can include a first flow-channel hardware set 310A coupled (e.g., assembled, inserted, connected, or mounted) with a first flow channel 680A. The first flow-channel hardware set 310A can include valves 106E, 106F, and a sensor 108A. The first flow channel 680A can include flow path elements 420A, pressure sensors 440A, flow sensors 440B, and a UF filter 690A. A dashed line area can include a second flow-channel hardware set 310B coupled (e.g., assembled, inserted, connected, or mounted) with a second flow channel 680B. The second flow-channel hardware set 310B can include valves 106E, 106F, and a sensor 108B. The second flow channel 680B can include flow path elements 420B, pressure sensors 440A, flow sensors 440B, and a DF filter 690B. In some embodiments, the second flow-channel hardware set 310B can further include valves 106E in a dashed dotted line area 320.

The first flow channel 680A can be used for a processing step for UF/DF to process a biological sample received from a previous unit operation 640 (e.g., a same unit operation for UF/DF or a different unit operation for VF, Chrom, VI, or the like). An output from the first flow channel 680A can be an input to the second flow channel 680B. The second flow channel 680B can be used for a subsequent processing step (e.g., a different processing step) for UF/DF. An output from the second flow channel 680B can be a biological product or an input to a next unit operation 650 (e.g., a same unit operation for UF/DF or a different unit operation for VF, Chrom, VI or the like). In such a way, the flow-channel hardware sets 310 can allow the first and second flow channels 680 to operate in series such that fluid continuously flows into the first and second flow channels 680 for UF/DF, thereby allowing continuous processing between an inlet and an outlet of the universal skid 100 and/or between an inlet and an outlet of the single-use kit 130D for UF/DF. Additionally, at least by continuous processing as taught herein, the universal skid 100 can cause zero, reduced, or optimized (e.g., minimal) hold-up volume for UF/DF, zero, reduced, or optimized (e.g., minimal) mean residence time in the surge vessel 120 and/or flow channels 680, and/or zero, reduced, or optimized (e.g., minimal) volume of the surge vessel 120 and/or flow channels 680. For example, mean residence time of the surge vessel 120 and/or flow channels 680 can be less than about 30 minutes (e.g., about 10 minutes to about 30 minutes). In another example, mean residence time of the surge vessel 120 and/or flow channels 680 can be less than about 60 minutes (e.g., about 40 minutes to about 60 minutes). In some embodiments, mean residence time of the surge vessel 120 and/or flow channels 680 can be less than about 120 minutes. The shortened or limited mean residence time can cause a reduction in the hold-up volume and volume of the surge vessel 120 and/or flow channels 680. Further, at least because of reduction in mean residence time, the universal skid 100 can allow the surge vessel 120 to receive and send flow at the same time, and/or allow more flexible use of the surge vessel 120 (e.g., allowing use of different quantities, different sizes, different arrangements, or different volumes of surge vessels).

In some embodiments, the UF/DF processing steps can be changed to be chromatography steps by changing from UF/DF filters 690 to chromatographic membranes/resins. Thus, FIG. 6D can also be a depiction of continuous chromatography in series.

Figure 7:
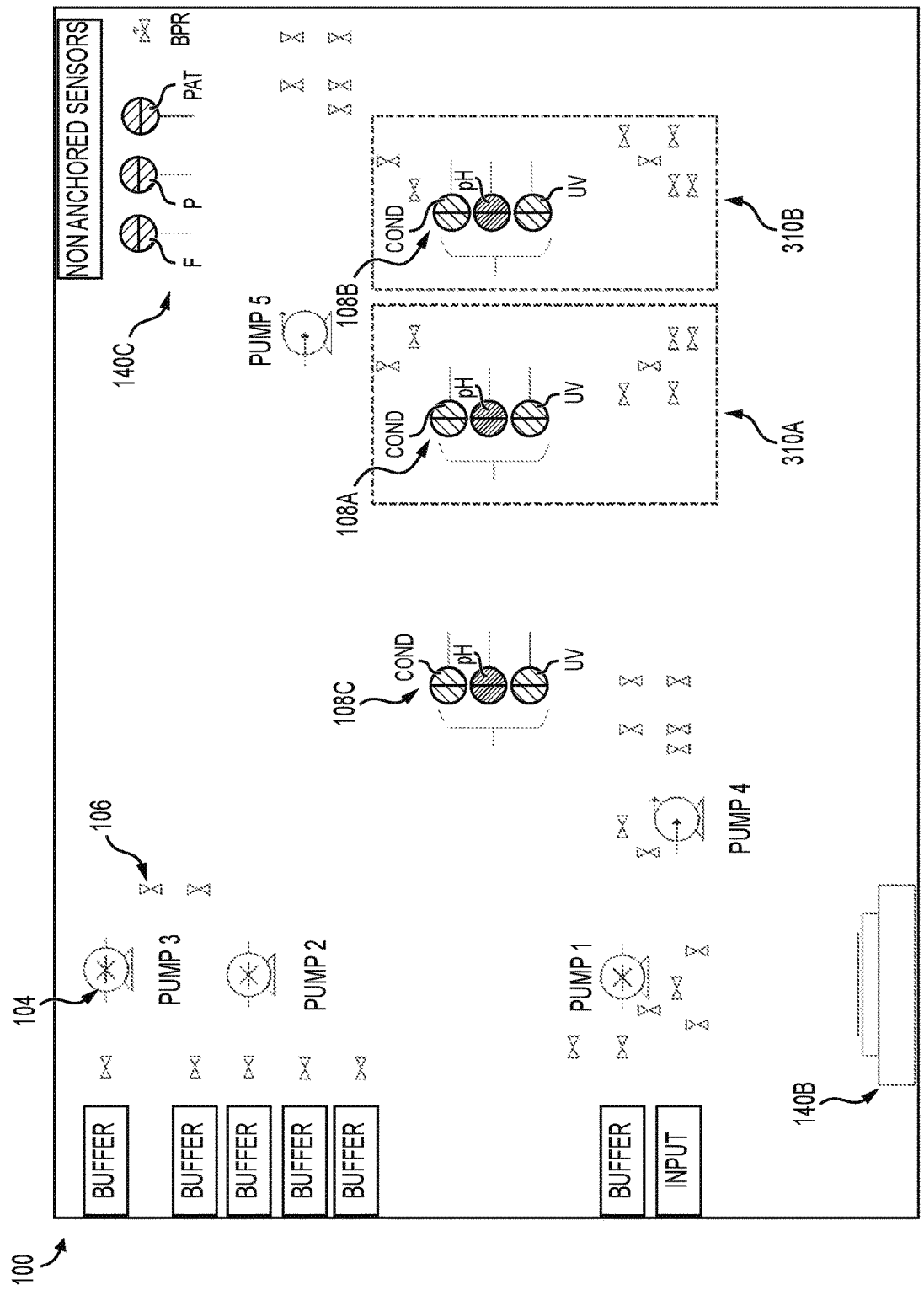
FIG. 7 is a P&ID illustrating another example universal skid in accordance with some embodiments.

FIG. 7 is a P&ID illustrating another example universal skid 100 disclosed herein. The universal skid 100 includes valves 106, sensors 108 (e.g., UV, pH, conductivity sensors 108A, 108B for flow-channel hardware sets 310A and 310B and a UV, pH, conductivity sensor 108C for a feed line), pumps 104 and regulators 140C. The flow-channel hardware sets 310 are configured to support flow channels. The universal skid 100 illustrated in FIG. 7 can have different quantities and positions for hardware components than those of a universal skid 100 illustrated in FIGS. 3-6.

Figure 8A:
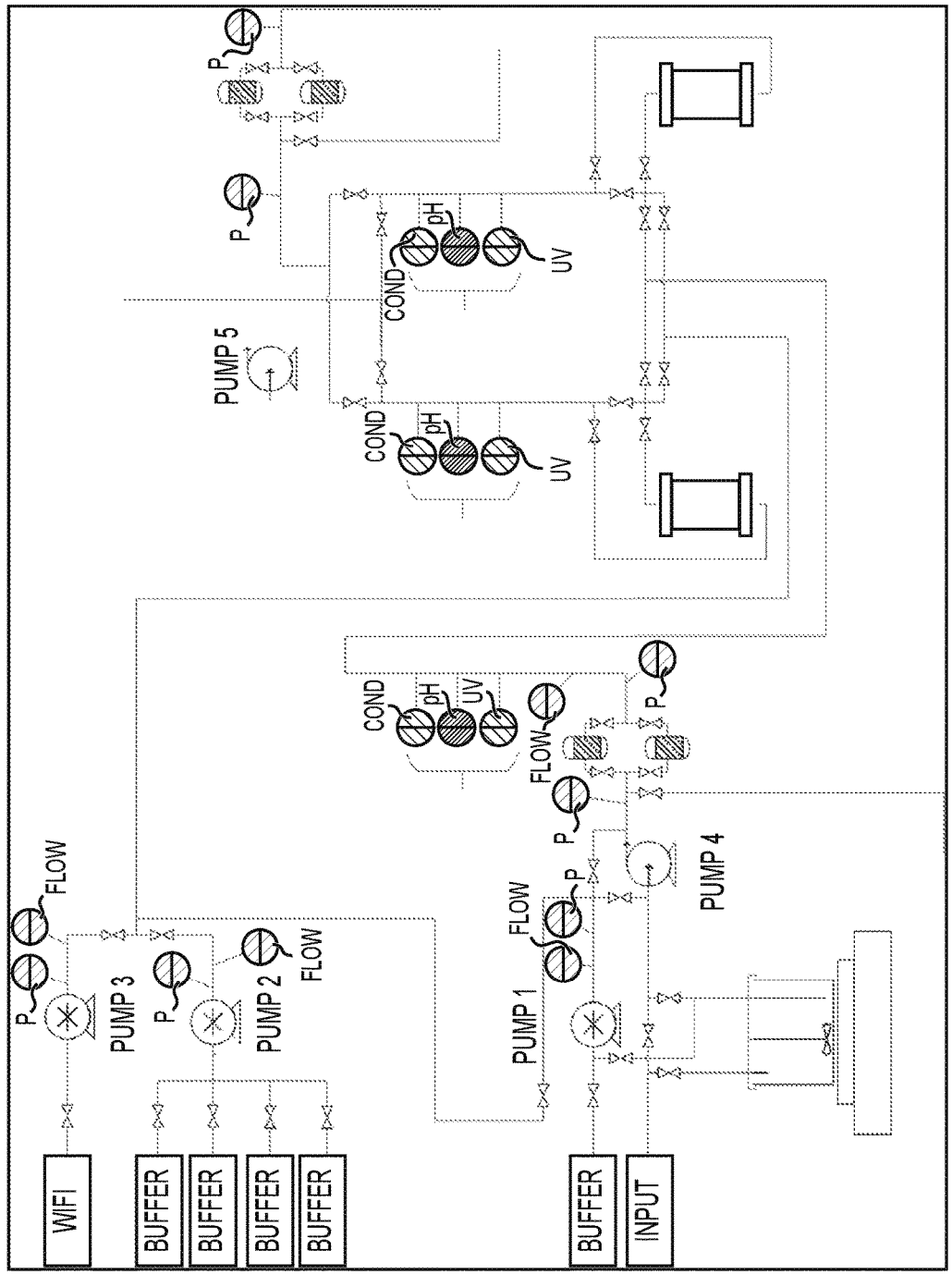
FIG. 8A is a P&ID illustrating a modular assembly for chromatography in accordance with some embodiments.
Figure 8B:
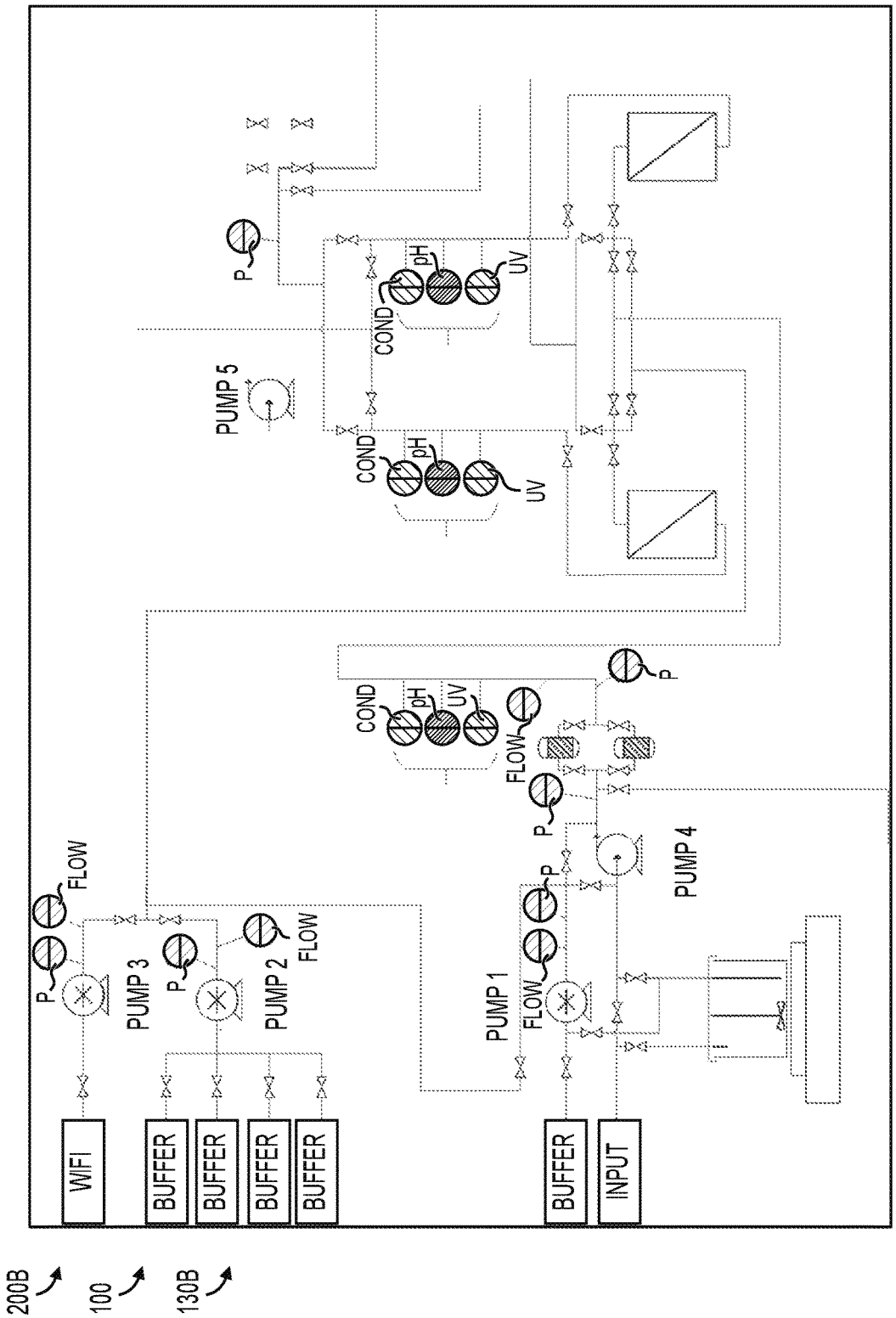
FIG. 8B is a P&ID illustrating a modular assembly for viral filtration in accordance with some embodiments.
Figure 8C:
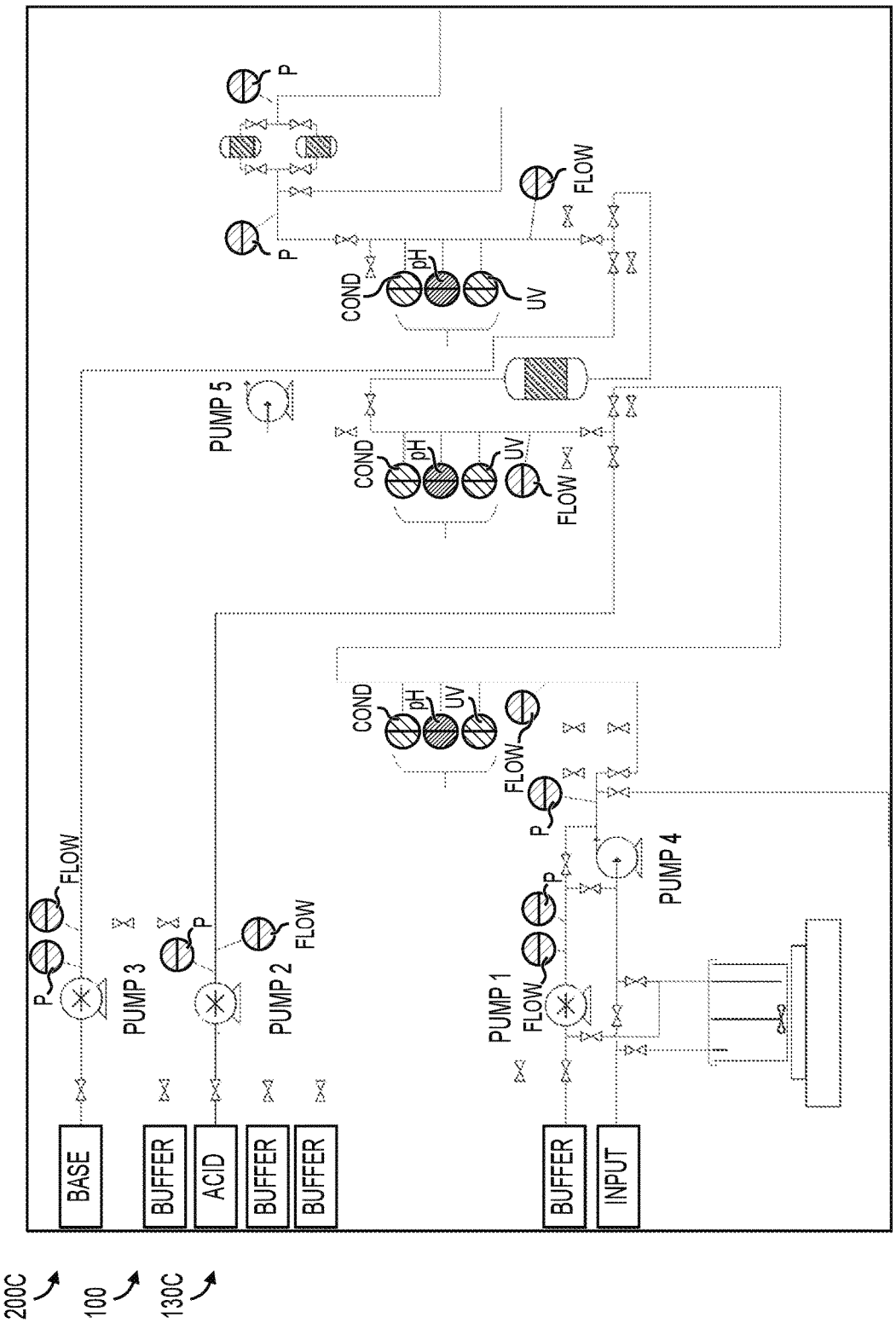
FIG. 8C is a P&ID illustrating a modular assembly for virus inactivation in accordance with some embodiments.
Figure 8D:
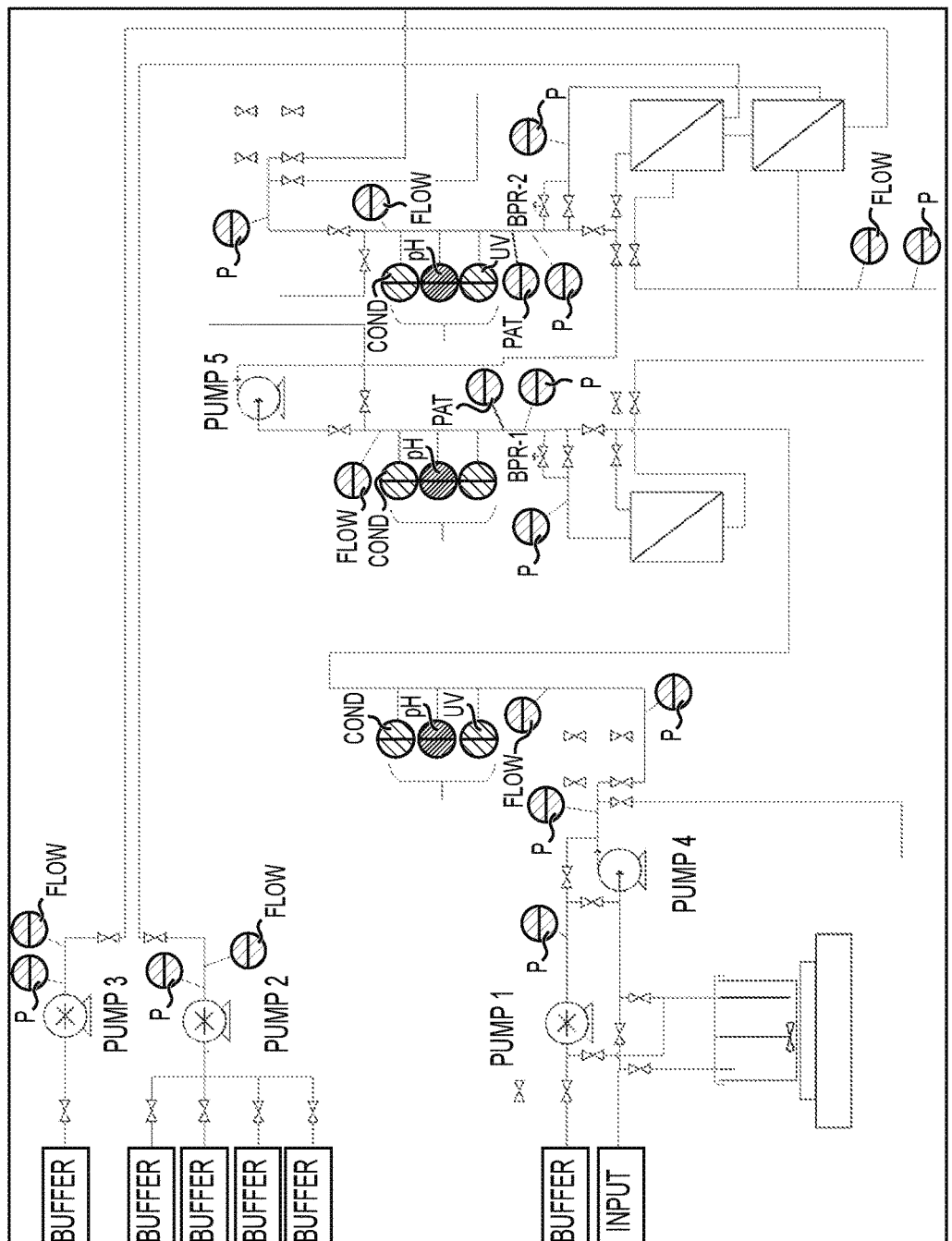
FIG. 8D is a P&ID illustrating a modular assembly for ultrafiltration/diafiltration in accordance with some embodiments.

FIG. 8A is a P&ID illustrating a modular assembly 200A for multi-column chromatography. The modular assembly 200A can be a universal skid 100 as illustrated in FIG. 7 coupled (e.g., assembled, connected, mounted, or inserted) with a single-use kit 130A for multi-column chromatography. FIG. 8B is a P&ID illustrating a modular assembly 200B for VF. The modular assembly 200B can be a universal skid 100 as illustrated in FIG. 7 coupled with a single-use kit 130B for VF. FIG. 8C is a P&ID illustrating a modular assembly 200C for VI. The modular assembly 200C can be a universal skid 100 as illustrated in FIG. 7 coupled with a single-use kit 130C for VI. FIG. 8D is a P&ID illustrating a modular assembly 200D for UF/DF. The modular assembly 200D can be a universal skid 100 as illustrated in FIG. 7 coupled with a single-use kit 130D for UF/DF. As illustrated, the single-use kit 130D can have more than two filters.

In some embodiments (not illustrated), a modular assembly 200 can be an assembly having a universal skid 100 coupled with multiple single-use kits for multiple same or different unit operations. For example, a first flow channel can be part of a first single-use kit for a first unit operation (e.g., one of Chrom, VI, VF, UF/DF, or the like), and the second flow channel can be part of a second single-use kit for a second unit operation that can be the same as the first unit operation or can be different than the first unit operation. Both the first and second flow channels can be coupled with a universal skid 100.

It should be understood that positions and quantities of hardware components of a universal skid can be different than the universal skids 100 illustrated in FIGS. 3-8. It should be also understood that hardware components of flow-channel hardware sets 310 can be different than those illustrated in FIGS. 3-8. Hardware components of a first flow-channel hardware set can be different than a second flow-channel hardware set. It should be also understood that a universal skid can have more than two flow-channel hardware sets for more than two flow channels. It should be also understood that different hardware components of a universal skid can be used for different unit operations. For example, components of a single-use kit can be coupled to all or some hardware components of a universal skid.

Manufacturing System for Continuous Manufacturing

Figure 9:
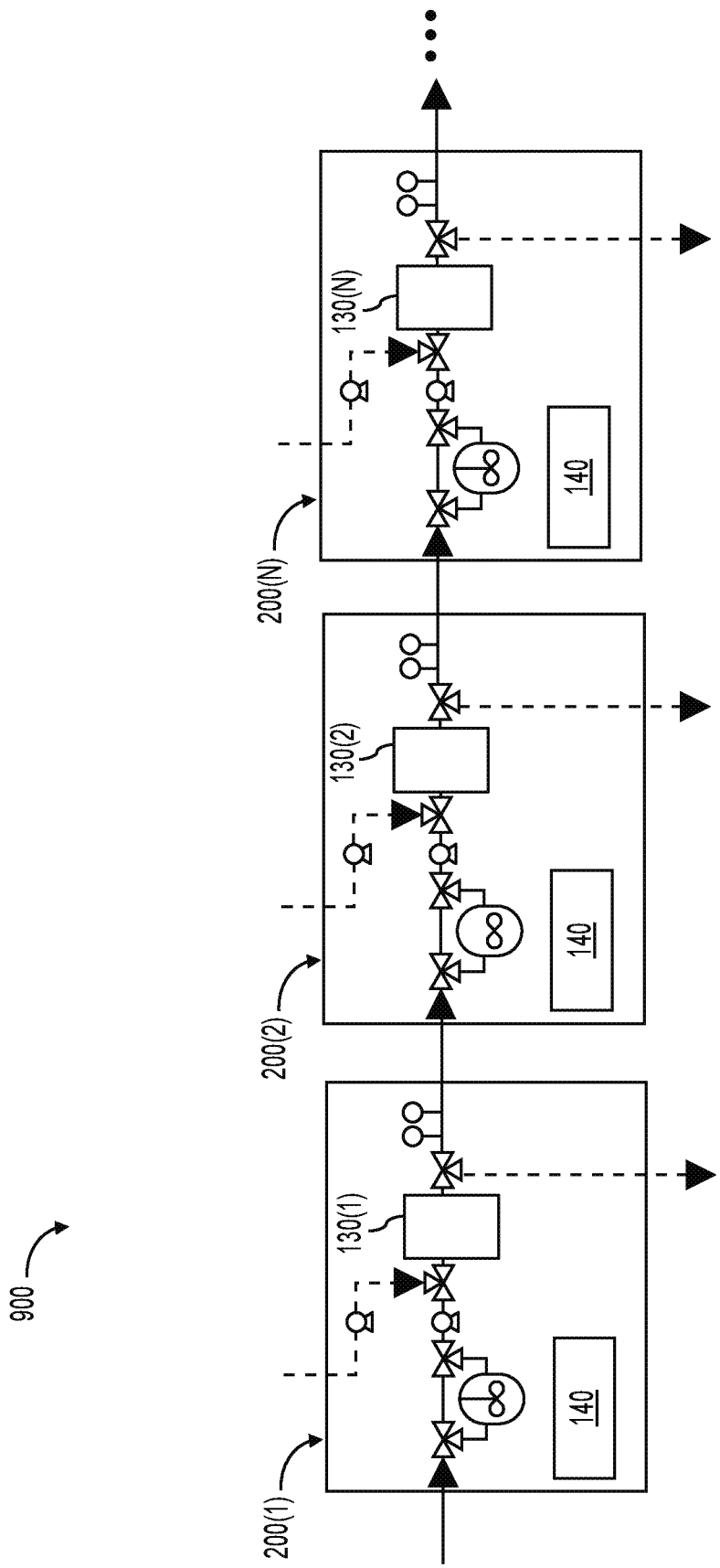
FIG. 9 is a diagram illustrating an example manufacturing system for continuous manufacturing in accordance with some embodiments.

FIG. 9 is a diagram illustrating an example manufacturing system 900 for continuous manufacturing of the present disclosure. The manufacturing system 900 can include multiple modular assemblies 200(1)-200(N) each performing a specific unit operation based on a corresponding single-use kit 130(1)-130(N). In some embodiments, the multiple modular assemblies 200(1)-200(N) can be different than each other. In some embodiments, some of modular assemblies 200(1)-200(N) can perform the same unit operation. Multiple modular assemblies can be coupled together, such as an output (e.g., outlet) of one modular assembly 200(1) can be coupled to an input (e.g., inlet) of a neighboring modular assembly 200(2) and so forth. Flow-channel hardware sets of the multiple modular assemblies can allow continuous processing within each of the multiple modular assemblies 200(1)-200(N), in between, fully continuous processing and/or end-to-end continuous processing from a start modular assembly 200(1) to an end modular assembly 200(N), fully continuous processing and/or end-to-end continuous processing across multiple unit operations. Flow-channel hardware sets of the multiple modular assemblies can cause zero, reduced, or optimized (e.g., minimal) internal hold-up volume within the multiple modular assemblies, zero, reduced, or optimized (e.g., minimal) mean residence time of one or more surge vessels and/or one or more flow channels used in the multiple modular assemblies, and/or zero, reduced, or optimized (e.g., minimal) volume of one or more surge vessels and/or one or more flow channels used in multiple modular assemblies. For example, mean residence time of one or more surge vessels and/or one or more flow channels used can be less than about 30 minutes (e.g., about 10 minutes to about 30 minutes). In another example, mean residence time of one or more surge vessels and one or more flow channels used can be less than about 60 minutes (e.g., about 40 minutes to about 60 minutes). In some embodiments, mean residence time of one or more surge vessels and one or more flow channels used can be less than about 120 minutes. The shortened or limited mean residence time can cause a reduction in the hold-up volume and volume of one or more surge vessels and one or more flow channels used. Further, at least because of reduction in mean residence time, one or more surge vessels can receive and send flow at the same time, and/or use of one or more surge vessels can become more flexible, (e.g., allowing use of different quantities, different sizes, different arrangements, or different volumes of surge vessels).

For example, with respect to FIGS. 6A-6D, as described above, the modular assemblies 200A-200D can be coupled together, such as an outlet (e.g., an outlet 510, 550, 610, 650) of one modular assembly of the modular assemblies 200A-200D can be coupled with an inlet (e.g., an outlet 500, 540, 600, 640) of another modular assembly of the modular assemblies 200A-200D and so forth. For each modular assembly 200, flow-channel hardware sets 310 can allow continuous processing between an inlet and an outlet of each modular assembly 200 and end-to-end continuous processing over a specific unit operation (e.g., Chrom, VF, VI, UF/DF). The flow-channel hardware sets 310 can cause zero, reduced, or optimized (e.g., minimal) internal hold-up volume within a corresponding modular assembly 200, zero, reduced, or optimized (e.g., minimal) mean residence time of a surge vessel 120 and/or flow channels, and/or zero, reduced, or optimized (e.g., minimal) volume of the surge vessel 120 and/or flow channels 460, 560, 660, 680. For combined modular assemblies 200A-200D, the flow-channel hardware sets 310 can further allow continuous processing in between the multiple modular assemblies 200A-200D, end-to-end continuous processing from a start modular assembly to an end modular assembly, and end-to-end continuous processing across multiple unit operations (e.g., Chrom, VF, VI, UF/DF).

In some embodiments, multiple modular assemblies 200(1)-200(N) can be coupled together contiguously, such as one modular assembly can be coupled to another modular assembly directly. In some embodiments, multiple modular assemblies can be coupled together with other processing steps in between. For example, one modular assembly can be coupled to one or more processing steps before it is coupled to another modular assembly. In some embodiments, for different types of processes, multiple modular assemblies 200(1)-200(N) at different scales (e.g., different holding different liquid volumes, sizes of modular assemblies, and/or quantities of hardware components) can be used to process volumes from a small size to a large size. Example implementations of the manufacturing system 900 using modular assemblies 200(1)-200(N) at different scales are described with respect to FIGS. 10A-10C.

Figure 10A:
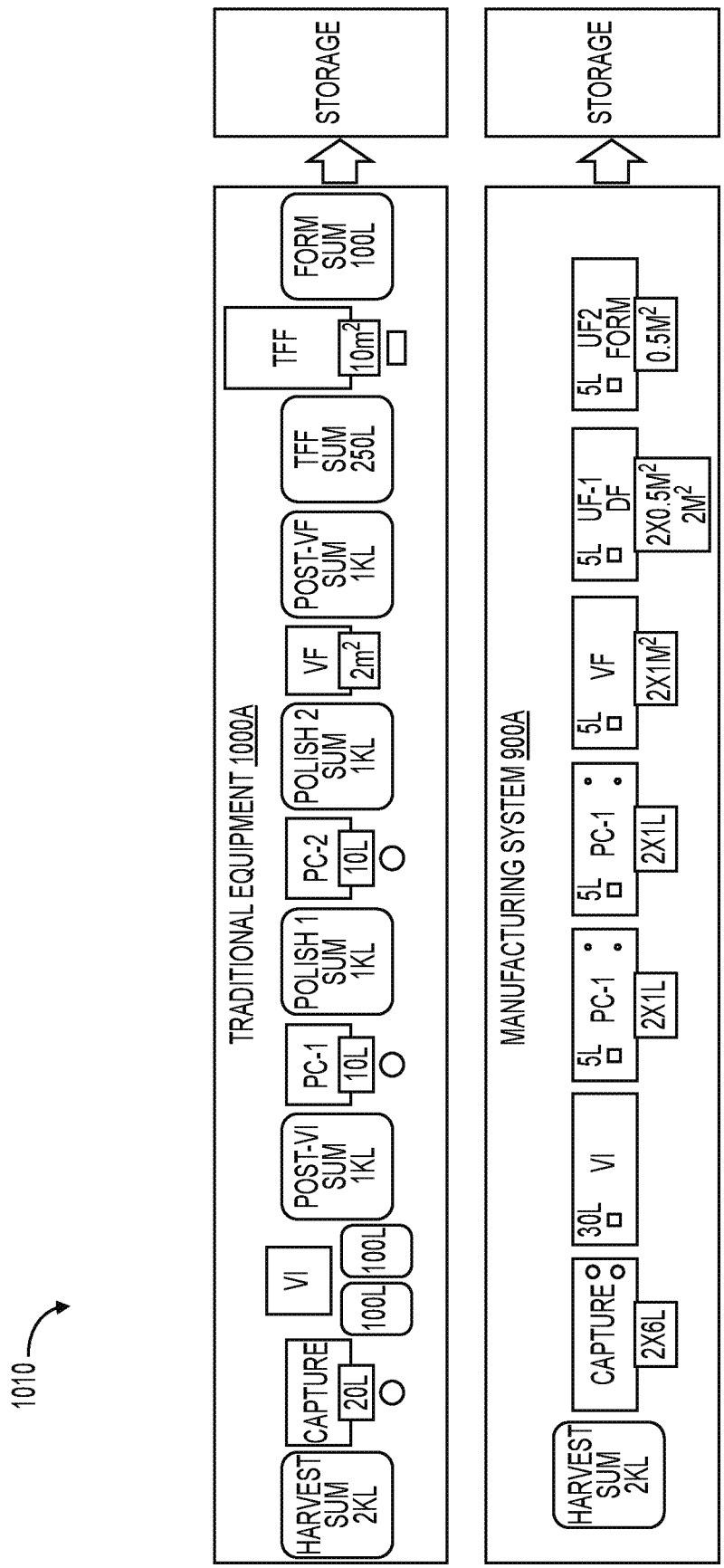
FIG. 10A is a diagram illustrating an example implementation of a manufacturing system for a fed-batch process in accordance with some embodiments.

FIG. 10A is a diagram illustrating an example implementation of a manufacturing system 900A for a fed-batch process 1010 (e.g., 2 kL fed-batch process @ 5 g/L). Compared with traditional equipment 1000A, the manufacturing system 900A uses modular assemblies at different scales (e.g., holding different liquid volumes labeled in FIG. 10A) for continuous processing with fewer steps and less equipment, which can reduce the equipment size, service and maintenance, and capital cost and provide other technical benefits as described above.

Figure 10B:
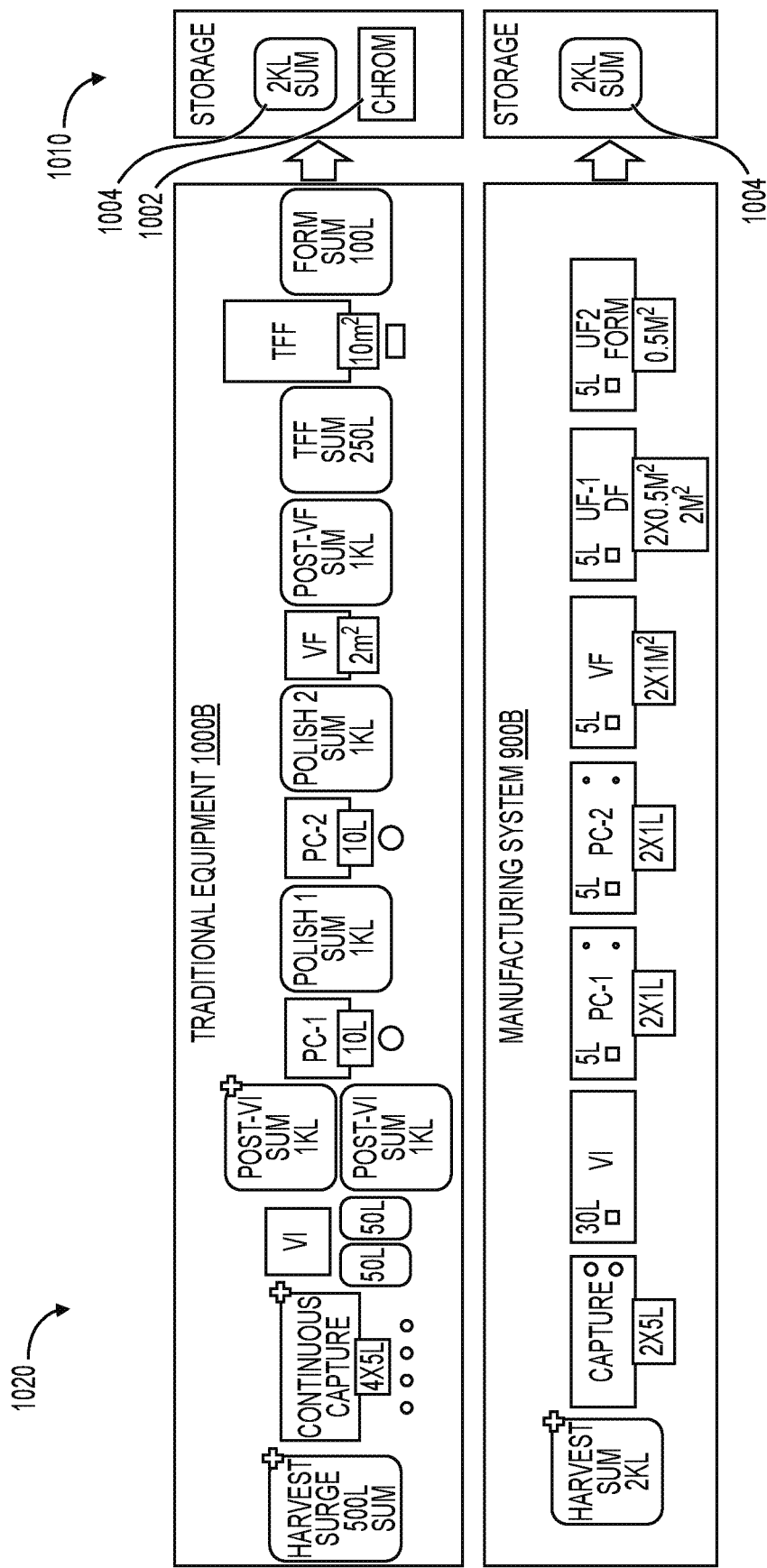
FIG. 10B is a diagram illustrating an example implementation of a manufacturing system for a perfusion process in accordance with some embodiments.

FIG. 10B is a diagram illustrating an example implementation of a manufacturing system 900B for a perfusion process 1020 (e.g., 500 L perfusion process @ 2.5 g/L/day). Compared with traditional equipment 1000B, the manufacturing system 900B uses modular assemblies at different scales (e.g., holding different liquid volumes labeled in FIG. 10B) for continuous processing with fewer steps and less equipment and with zero or minimal hold-up volume (e.g., temporal or intermediate storage). FIG. 10B also illustrates additional equipment that can be used to conduct the fed-batch process 1010 in the same area (noted in "Storage"). To conduct the fed-batch process 1010, the manufacturing system 900B can use one extra piece of equipment: a 2000 L single-use mixer ("2 kL SUM") 1004. In contrast, the traditional equipment 1000B requires two extra pieces of equipment: a 2000 L single-use mixer ("2 kL SUM") 1004 and a chromatography skid ("Chrom") 1002.

Figure 10C:
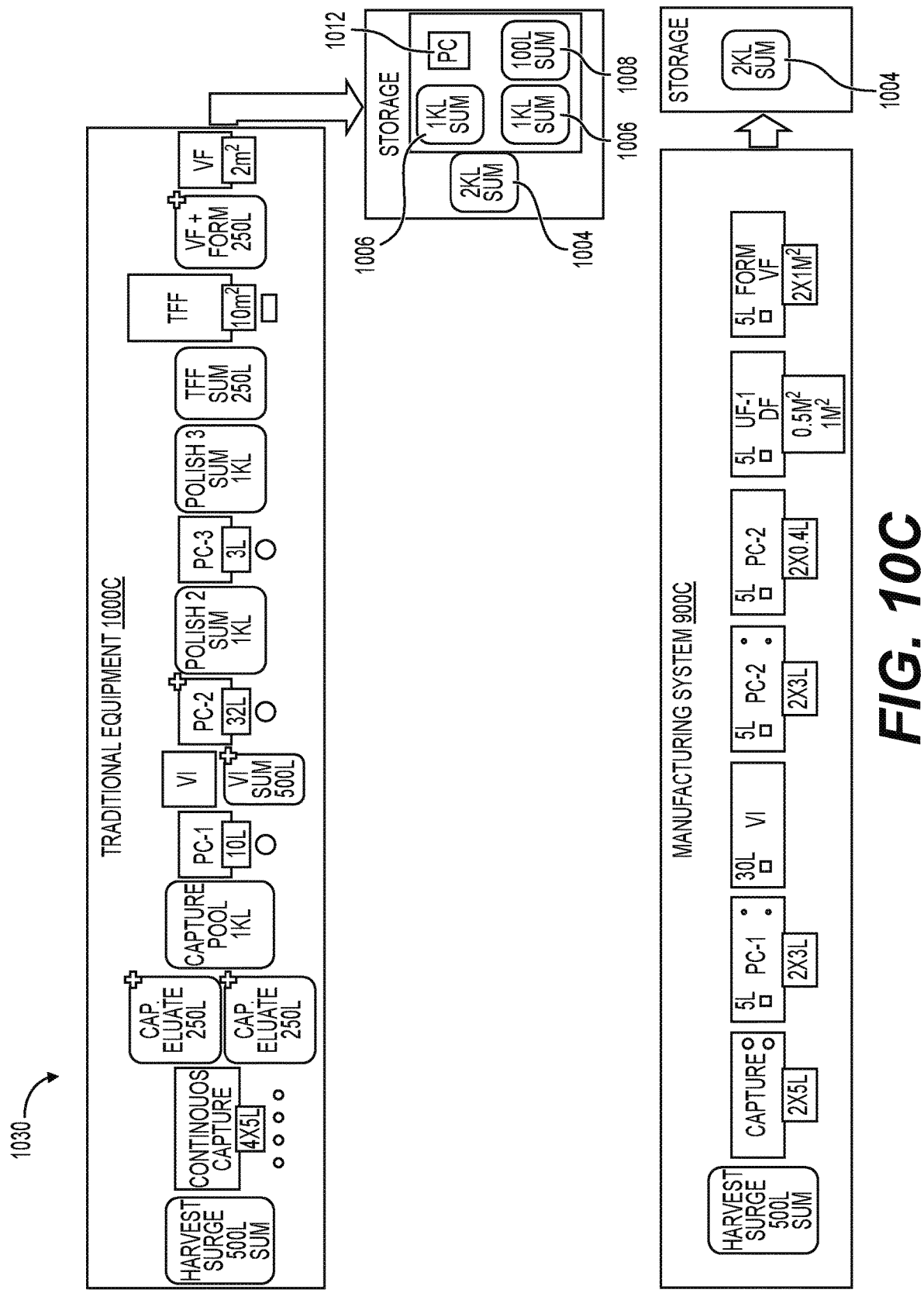
FIG. 10C is a diagram illustrating an example implementation of a manufacturing system for a perfusion process in accordance with some embodiments.

FIG. 10C is a diagram illustrating an example implementation of a manufacturing system 900C for a perfusion process 1030 (e.g., 500 L perfusion process @ 0.5 g/L/day). Compared with traditional equipment 1000C, the manufacturing system 900C uses modular assemblies at different scales (e.g., holding different liquid volumes labeled in FIG. 10C) for continuous processing with fewer steps and less equipment and with zero or minimal hold-up volume (e.g., temporal or intermediate storage). FIG. 10C also illustrate additional equipment that can be used to conduct the fed-batch process 1010 and the perfusion process 1020 in the same area (noted in "Storage"). To conduct the fed-batch process 1010 and perfusion process 1020, the manufacturing system 900C can use one extra piece of equipment: a 2000 L single-use mixer ("2 kL SUM") 1004. In contrast, the traditional equipment 1000C requires five extra pieces of equipment: a 2000 L single-use mixer ("2 kL SUM") 1004, two 1000 L single-use mixers ("1 kL SUM") 1006, one 100 L single-use mixer ("100 L SUM") 1008 and a polishing chromatography skid ("PC") 1012.

Figure 11A:
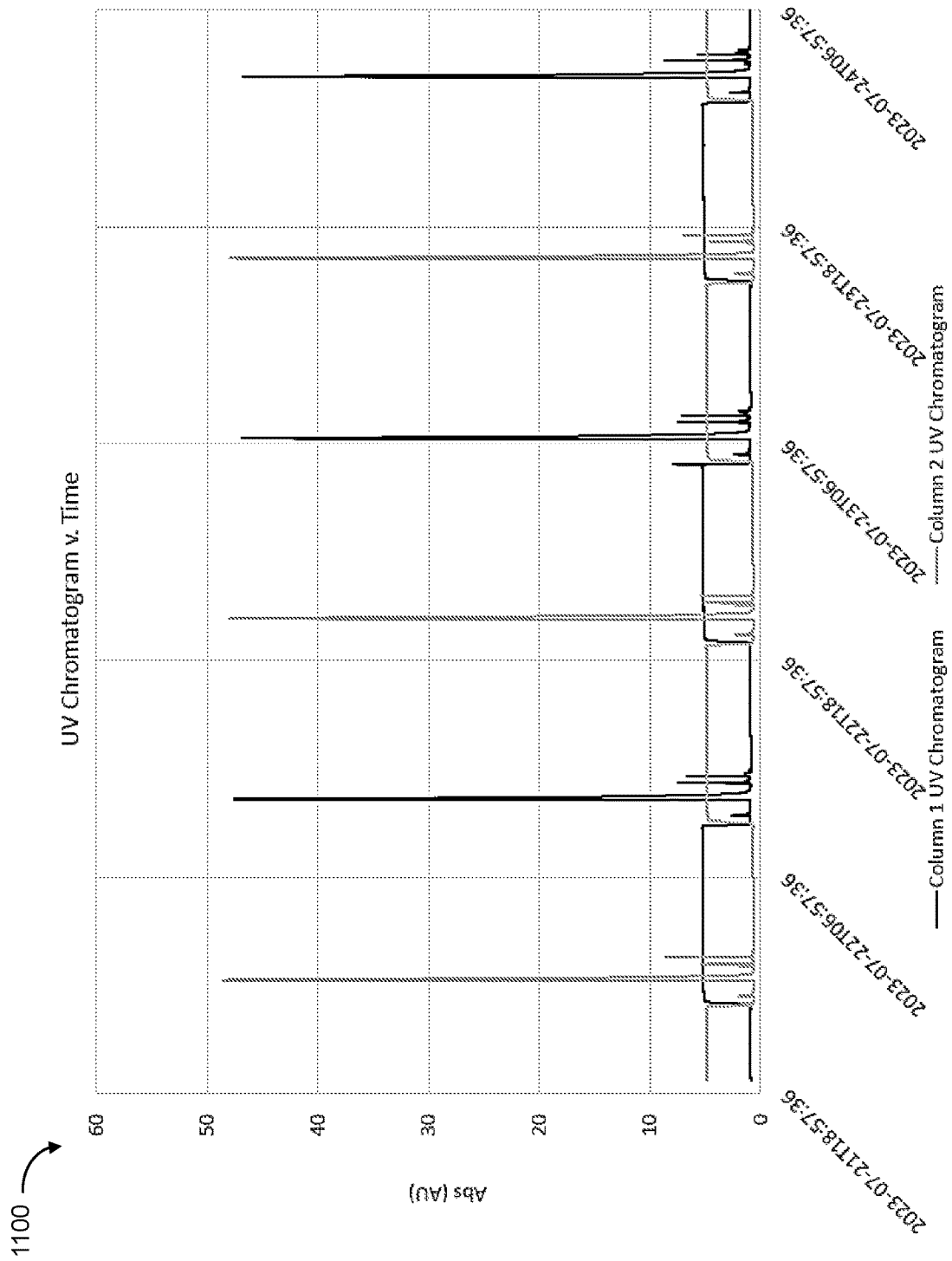
FIG. 11A is a diagram illustrating a plot of absorbance values versus time for each flow channel of an example modular assembly for chromatography.
Figure 11B:
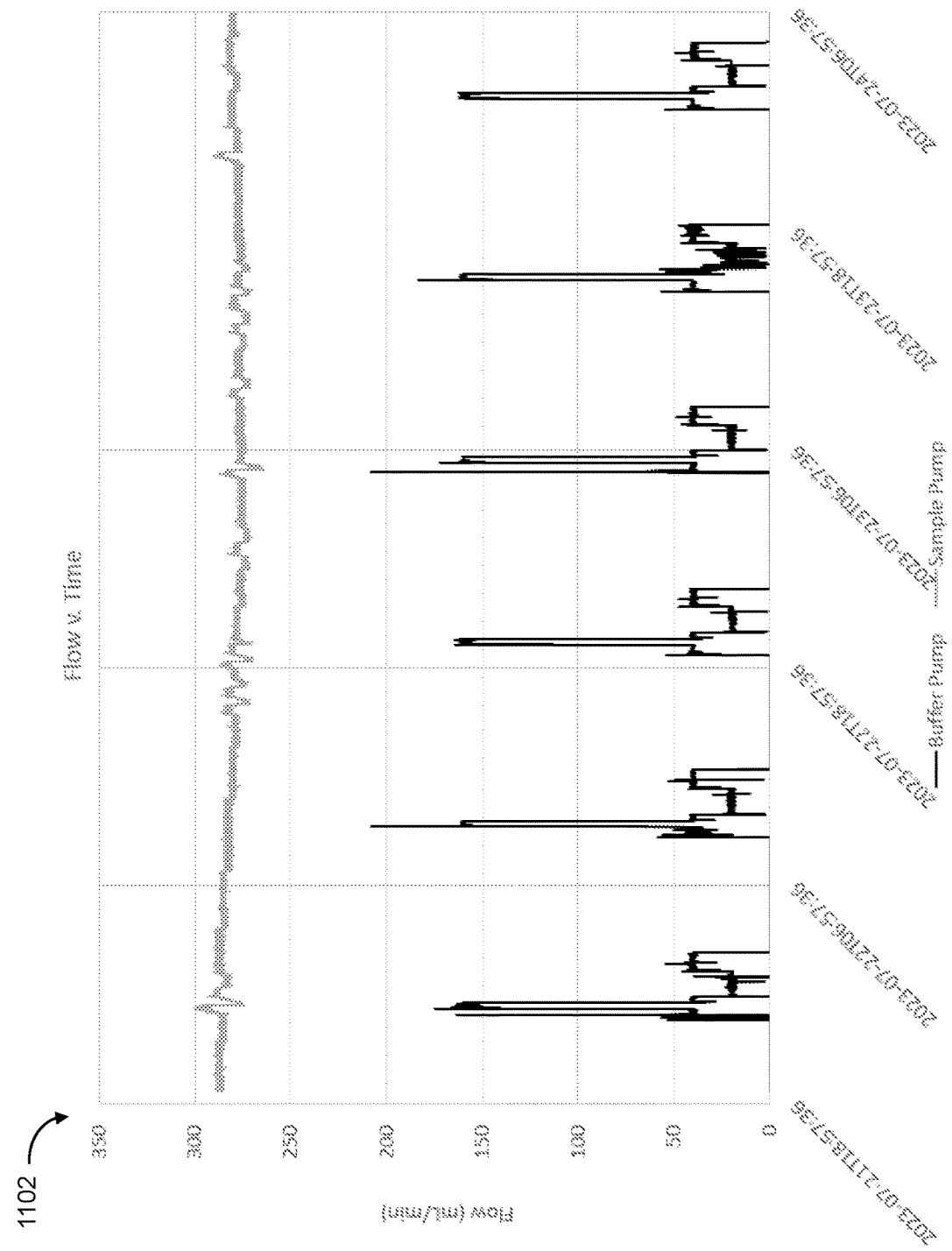
FIG. 11B is a diagram illustrating a plot of flow rates versus time for buffers and samples of an example modular assembly for chromatography.
Figure 11C:
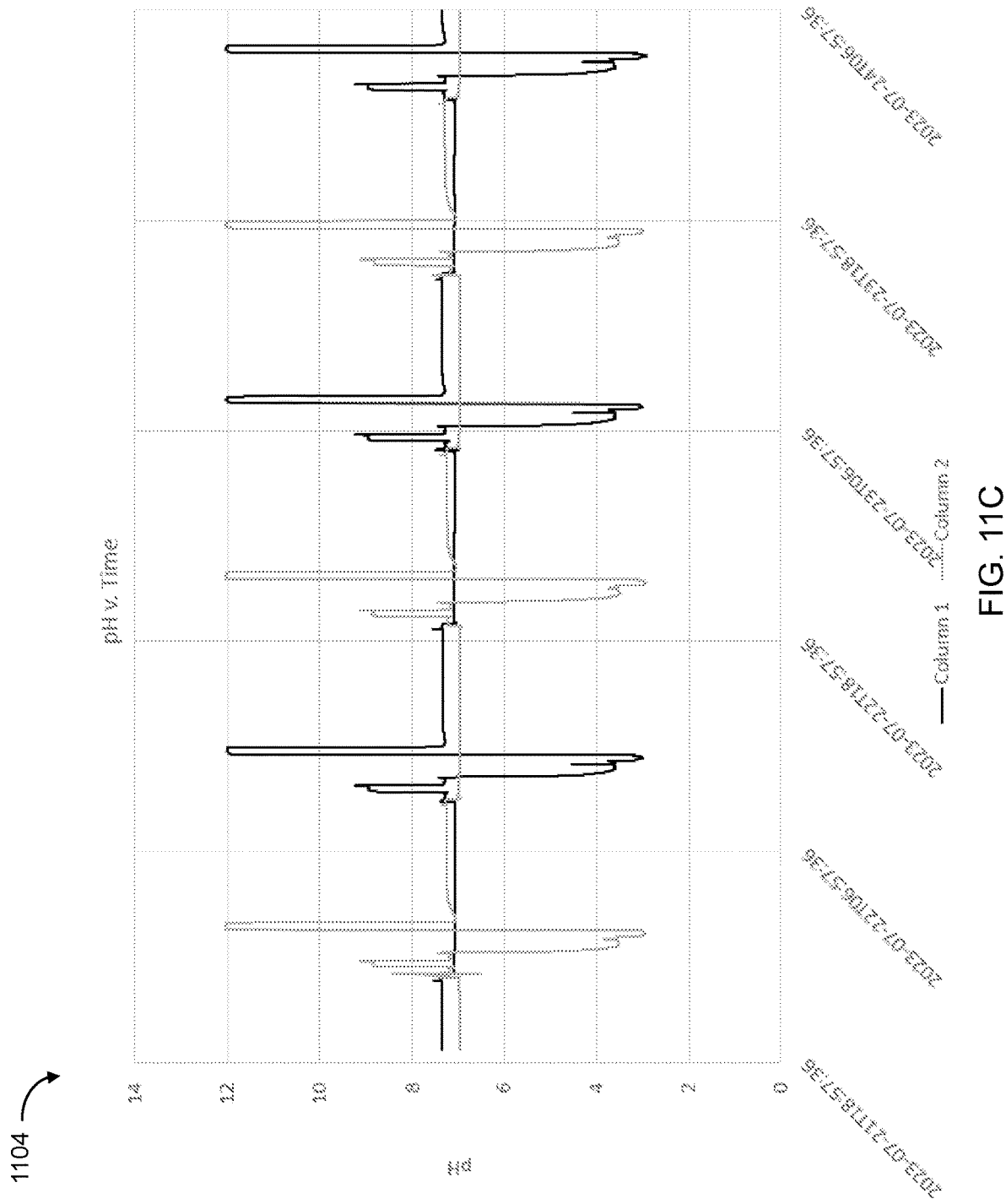
FIG. 11C is a diagram illustrating a plot of pH values versus time for each flow channel of an example modular assembly for chromatography.
Figure 11D:
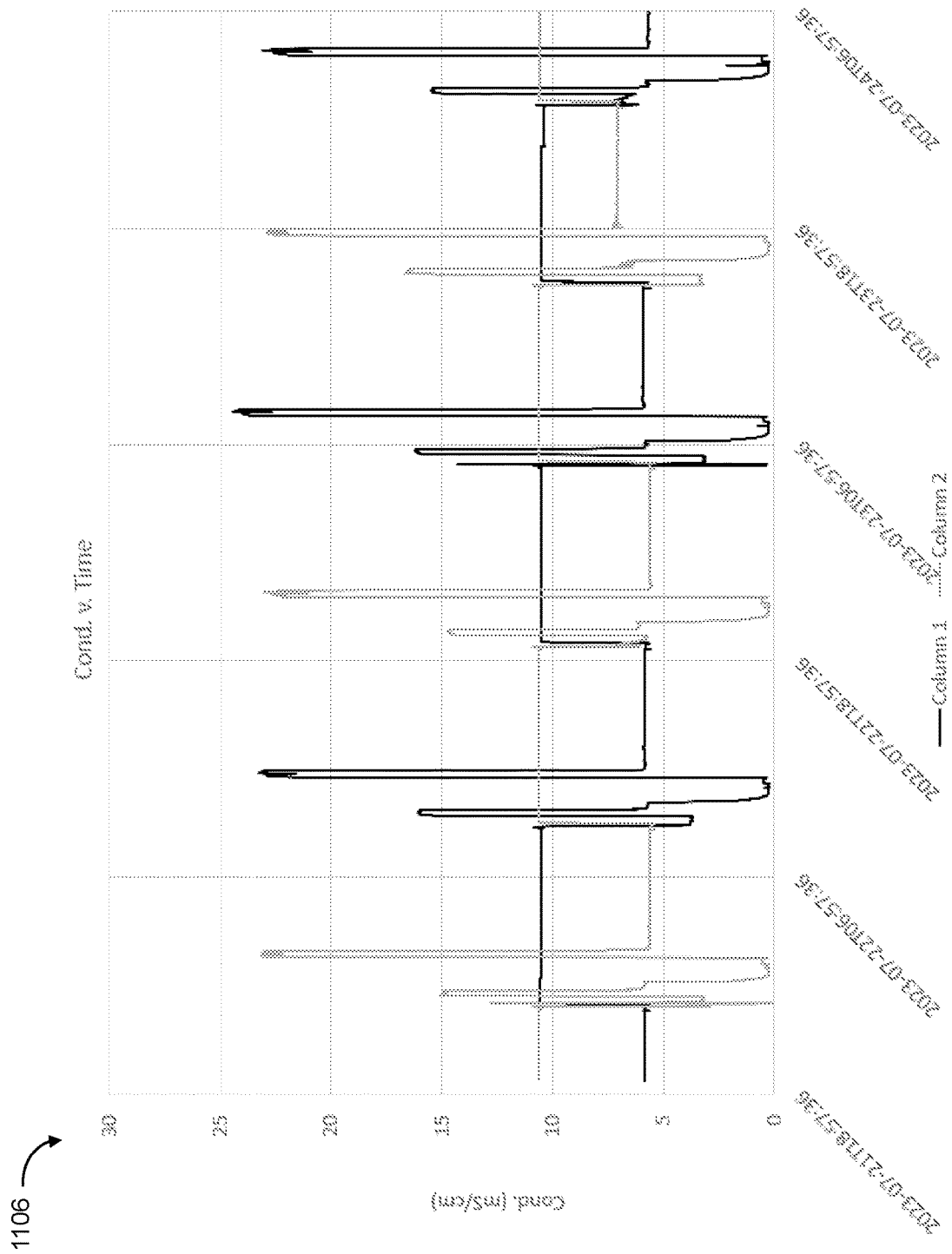
FIG. 11D is a diagram illustrating a plot of conductivity values versus time for each flow channel of an example modular assembly for chromatography.

FIG. 11A is a diagram illustrating a plot 1100 of absorbance values versus time for each flow channel of an example modular assembly for chromatography. These results can be obtained from a modular assembly 200A as illustrated in FIG. 6A based on data captured by sensors 108A and 108B. FIG. 11B is a diagram illustrating a plot 1102 of flow rates versus time for buffers and samples of an example modular assembly for chromatography. These results can be obtained from a modular assembly 200A as illustrated in FIG. 6A based on data captured by flow sensors 440B. FIG. 11B also demonstrates how the modular assembly 200A operating with the two flow channels 460 in parallel allows for an inlet product stream to be continuously flowing. It should be understood that the same principle can apply for operations (such as VF or other filtrations) with the flow channels operating in parallel. FIG. 11C is a diagram illustrating a plot 1104 of pH values versus time for each flow channel of an example modular assembly for chromatography. These results can be obtained from a modular assembly 200A as illustrated in FIG. 6A based on data captured by sensors 108A and 108B. FIG. 11D is a diagram illustrating a plot 1106 of conductivity values versus time for each flow channel of an example modular assembly for chromatography. These results can be obtained from a modular assembly 200A as illustrated in FIG. 6A based on data captured by sensors 108A and 108B. All the results of FIGS. 11A-11D are as expected indicating that a modular assembly can perform a continuous processing for chromatography.

Figure 12A:
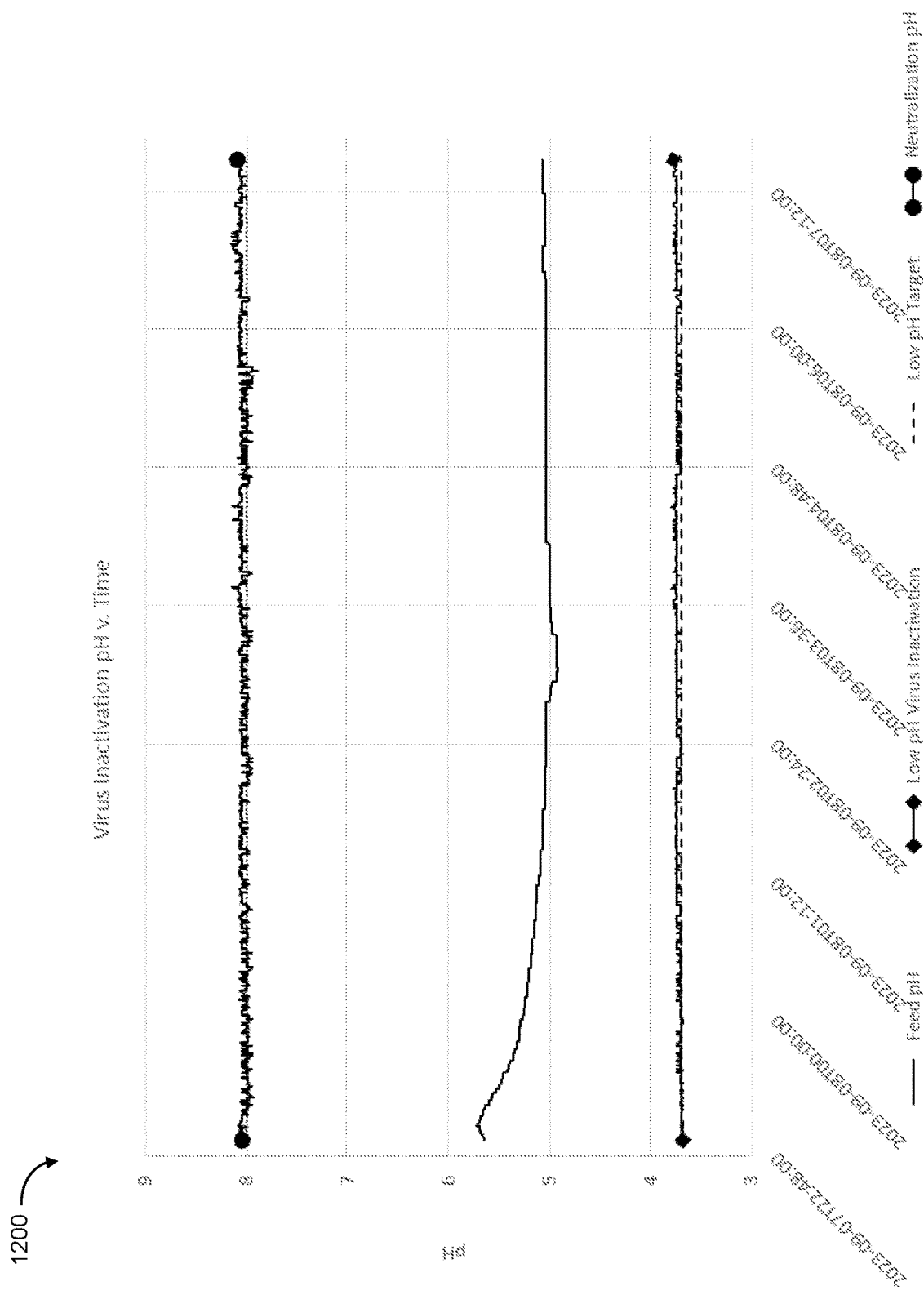
FIG. 12A is a diagram illustrating a plot of pH values versus time for each flow channel of an example modular assembly for virus inactivation.
Figure 12B:
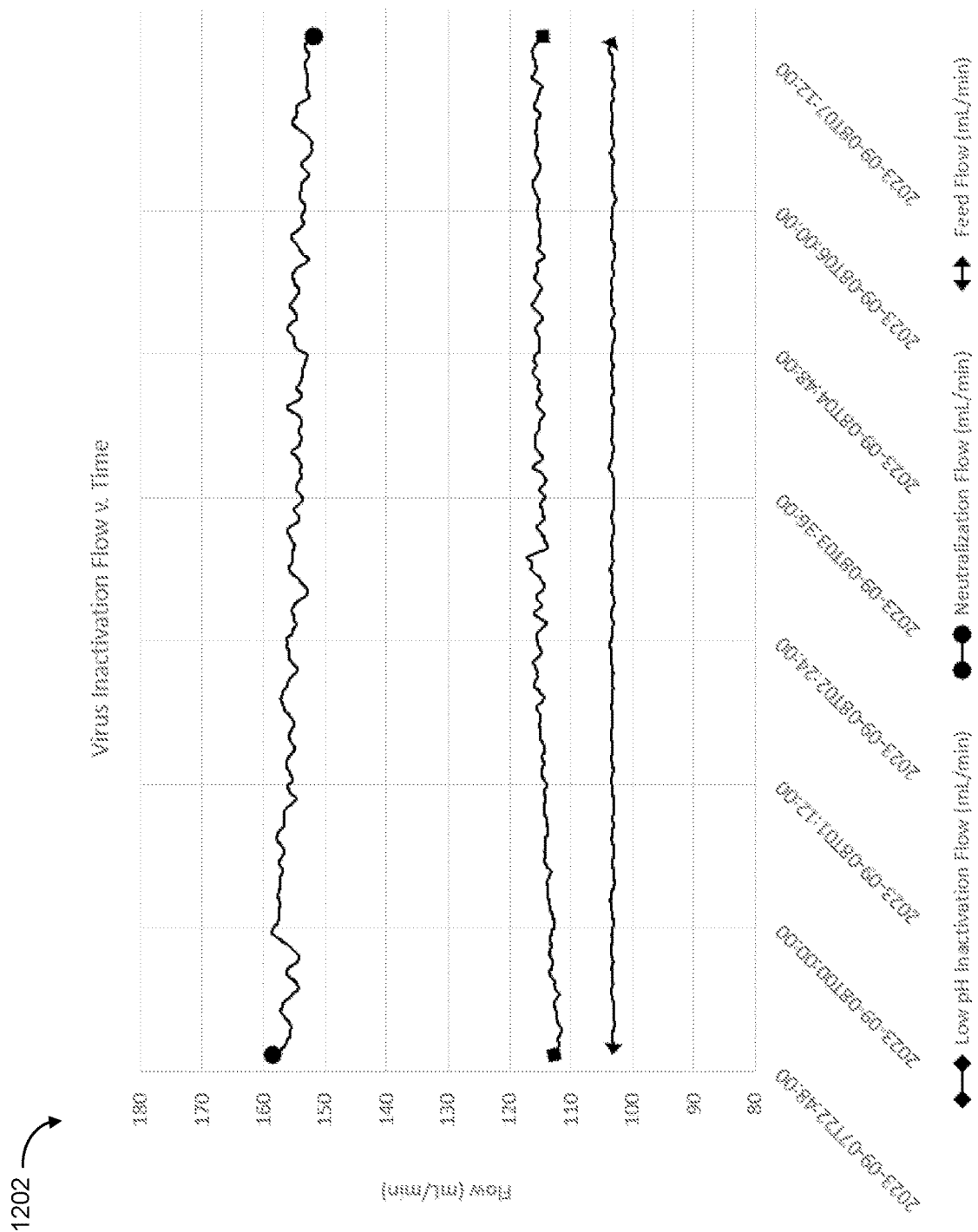
FIG. 12B is a diagram illustrating a plot of flow rates versus time for a feed line and each flow channel of an example modular assembly for virus inactivation.

FIG. 12A is a diagram illustrating a plot 1200 of pH values versus time for each flow channel of an example modular assembly for VI. These results can be obtained from a modular assembly 200C as illustrated in FIG. 6C based on data captured by sensors 108A-108C. For example, pH values for a feed line can be obtained using sensor 108C. Low pH values and neutralization pH values can be obtained using sensors 108A and 108B. FIG. 12B is a diagram illustrating a plot 1202 of flow rates versus time for a feed line and each flow channel of an example modular assembly for VI. These results can be obtained from a modular assembly 200C as illustrated in FIG. 6C based on data captured by flow sensors 440B of a feed line and each flow channel. All the results of FIGS. 12A-12B are as expected indicating that a modular assembly can perform a continuous processing for VI.

Figure 13A:
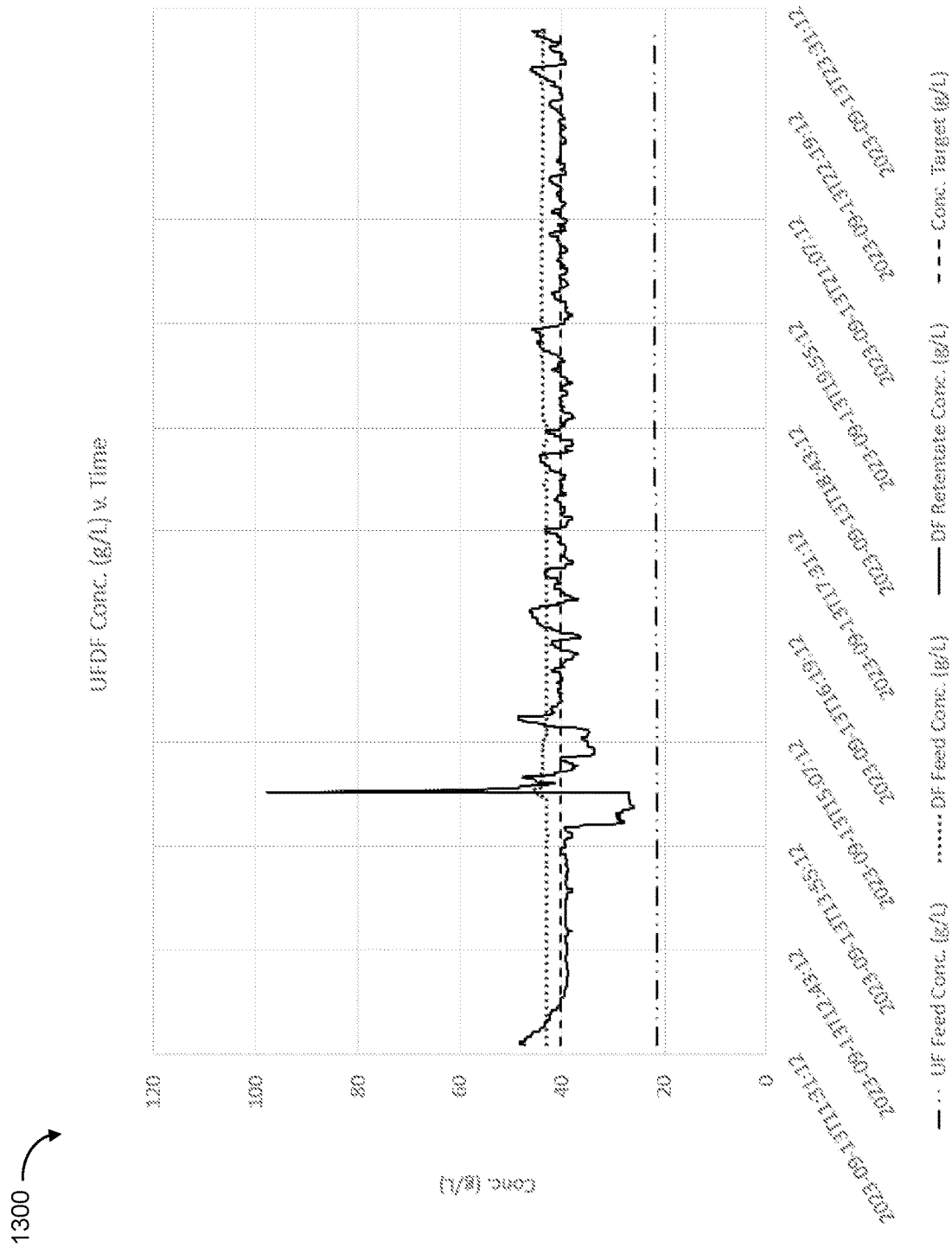
FIG. 13A is a diagram illustrating a plot of conductivity values versus time for each flow channel of an example modular assembly for ultrafiltration/diafiltration.
Figure 13B:
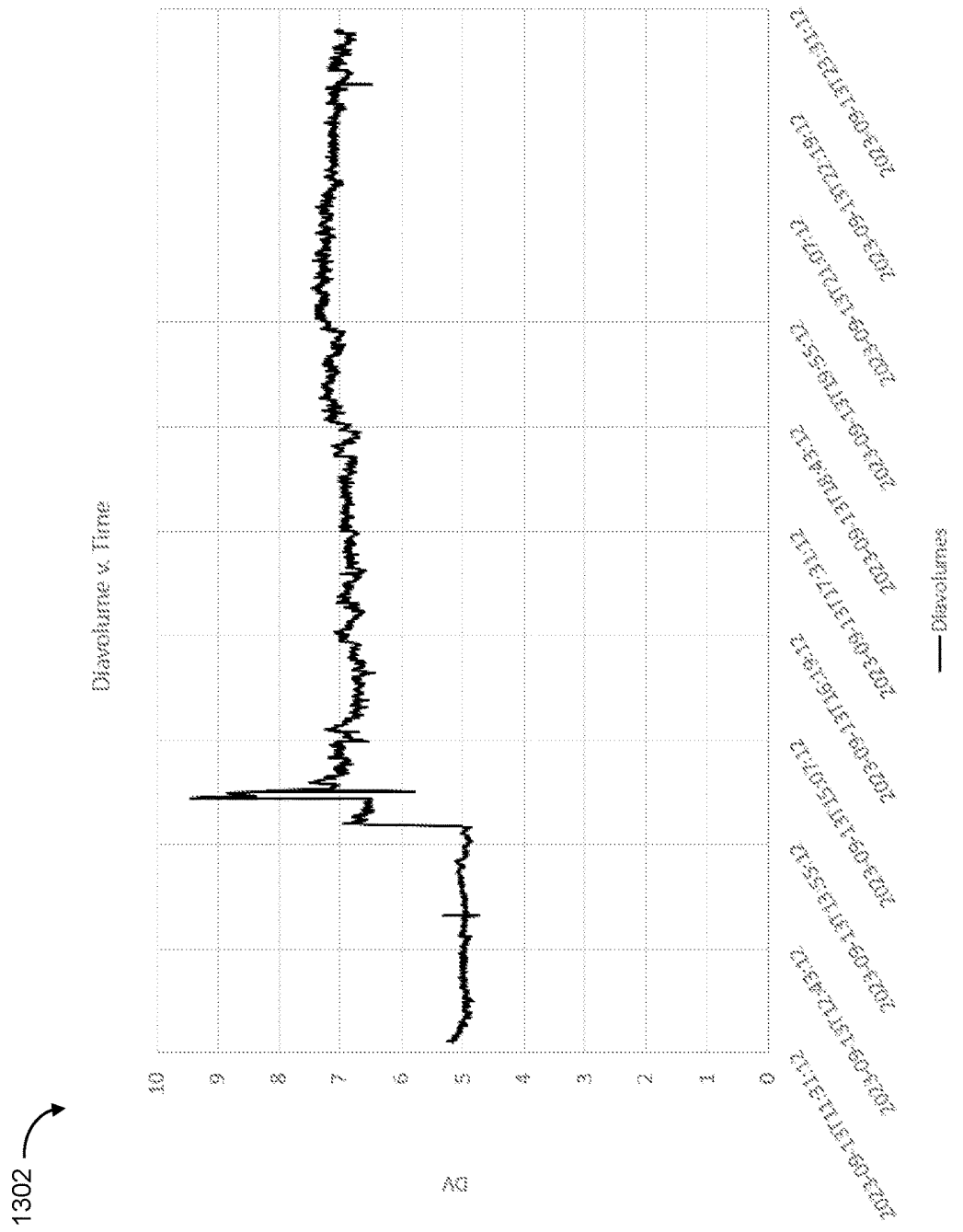
FIG. 13B is a diagram illustrating a plot of diavolume values versus time for each flow channel of an example modular assembly for ultrafiltration/diafiltration.
Figure 13C:
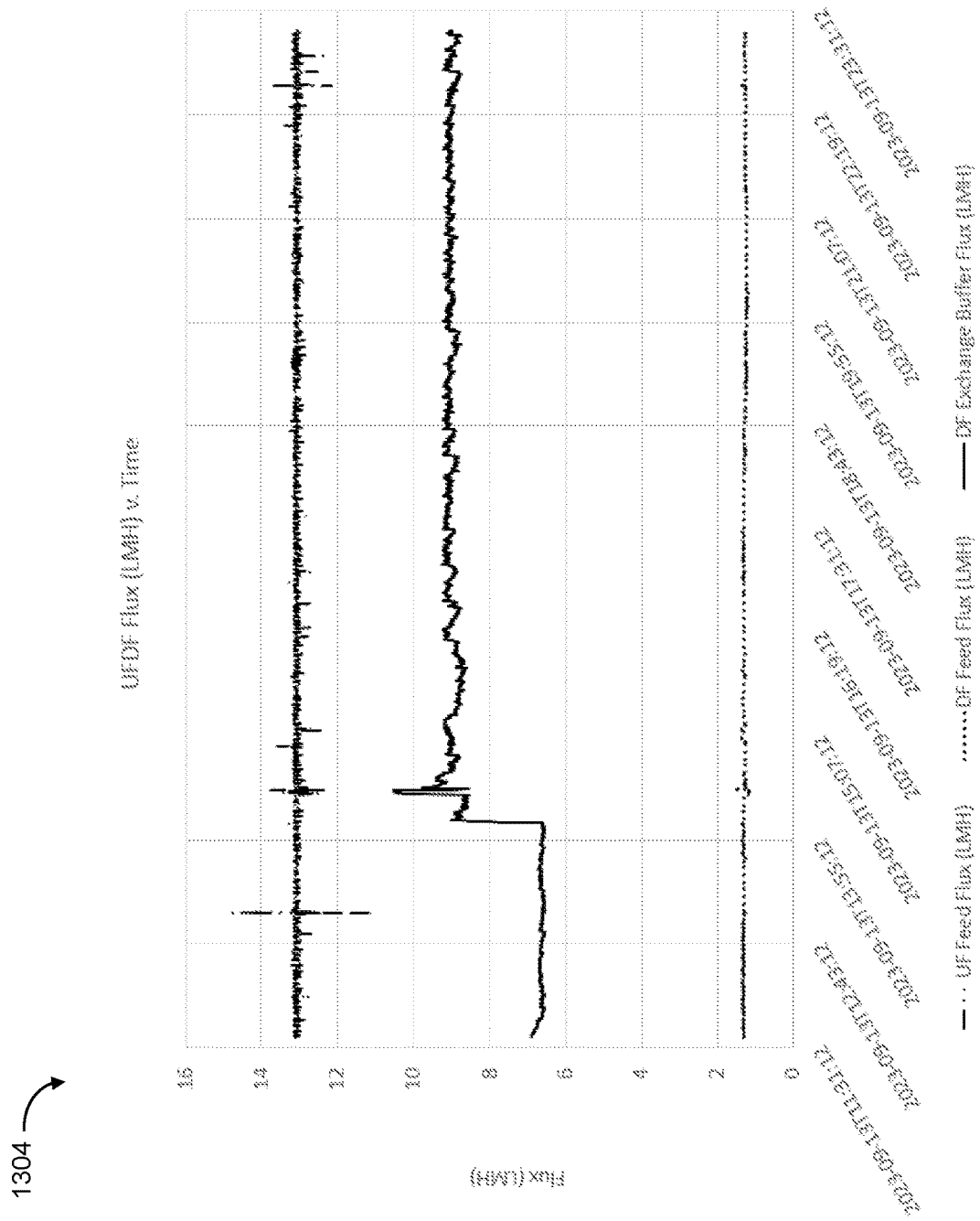
FIG. 13C is a diagram illustrating a plot of flux values versus time for each flow channel of an example modular assembly for ultrafiltration/diafiltration.

FIG. 13A is a diagram illustrating a plot 1300 of conductivity values versus time for each flow channel of an example modular assembly for UF/DF. These results can be obtained from a modular assembly 200D as illustrated in FIG. 6D based on data captured by sensors 108A-108B. FIG. 13B is a diagram illustrating a plot 1302 of diavolume values versus time for each flow channel of an example modular assembly for UF/DF. These results can be obtained from a modular assembly 200D as illustrated in FIG. 6D based on data captured by diavolume sensors 440C. FIG. 13C is a diagram illustrating a plot 1304 of flux values versus time for each flow channel of an example modular assembly for UF/DF. These results can be obtained from a modular assembly 200D as illustrated in FIG. 6D based on data captured by flow sensors 440B. All the results of FIGS. 13A-13C are as expected indicating that a modular assembly can perform a continuous processing for UF/DF.

In some embodiments, the systems disclosed herein (e.g., universal skid 100, modular assembly 200, manufacturing system 900) are closed systems. A closed system includes unit operations that are designed and operated to limit exposure to the outside environment. Materials may be introduced to a closed system, but the addition must be done in such a way to avoid exposure of the product to the room environment.

The systems described herein can also include a fluid conduit that is disposed between the apparatus and the unit operation. Suitable fluid conduits can be a tube that is made of polyethylene, polycarbonate, or plastic. The fluid conduits can also include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; and one or more filters that are disposed in the fluid conduit such that they are capable of filtering (e.g., removing bacteria) the fluid present in the fluid conduit.

In some embodiments, the systems provided herein include a pump system. A pump system can include one or more the following: one or more pumps as known in the art, one or more filters known in the art, and one or more UV detectors.

It should be understood that the operations and processes described above and illustrated in the figures can be carried out or performed in any suitable order as desired in various implementations. Additionally, in certain implementations, at least a portion of the operations can be carried out in parallel. Furthermore, in certain implementations, less than or more than the operations described can be performed.

In describing example embodiments, specific terminology is used for the sake of clarity. For purposes of description, each specific term is intended to at least include all technical and functional equivalents that operate in a similar manner to accomplish a similar purpose. Additionally, in some instances where a particular example embodiment includes multiple system elements, device components or method steps, those elements, components or steps may be replaced with a single element, component or step. Likewise, a single element, component or step may be replaced with multiple elements, components or steps that serve the same purpose. Moreover, while example embodiments have been shown and described with references to particular embodiments thereof, those of ordinary skill in the art will understand that various substitutions and alterations in form and detail may be made therein without departing from the scope of the present disclosure. Further still, other embodiments, functions and advantages are also within the scope of the present disclosure.

What is claimed is:

1. A universal skid for processing one or more biological products, comprising:
   a rigid support; and
   a plurality of flow-channel hardware sets mounted on the rigid support, each flow-channel hardware set configured to couple with replaceable components defining a respective flow channel of a plurality of flow channels for one or more unit operations of a production process for the one or more biological products,
   wherein at least one flow-channel hardware set of the plurality of flow-channel hardware sets is configured to couple with replaceable components defining a flow channel for one or more alternative unit operations of a production process for the one or more biological products,
   wherein at least one flow-channel hardware set of the plurality of flow-channel hardware sets includes components for supporting and controlling an ultrafiltration or diafiltration operation, and at least one flow-channel hardware set of the plurality of flow-channel hardware sets includes components supporting a chromatography operation;
   wherein the plurality of flow-channel hardware sets allow for continuous processing over the one or more unit operations.

2. The universal skid of claim 1, wherein the plurality of flow-channel hardware sets each comprise at least two of the same types of hardware components as each other, providing hardware support for allowing a first flow channel associated with a first processing step of the one or more unit operations and a second flow channel associated with a second processing step of the one or more unit operations arranged in an in-parallel configuration or an in-series configuration.

3. The universal skid of claim 1, wherein the plurality of flow-channel hardware sets allow the plurality of flow channels to operate in series for continuous processing over the one or more unit operations.

4. The universal skid of claim 1, wherein the plurality of flow-channel hardware sets allow the plurality of flow channels to operate in parallel for continuous processing over the one or more unit operations.

5. The universal skid of claim 1, wherein the plurality of flow-channel hardware sets cause zero or an optimized hold-up volume for the one or more unit operations.

6. The universal skid of claim 1, wherein the plurality of flow-channel hardware sets reduce mean residence time in one or more surge vessels or the plurality of flow channels used in a respective single-use kit coupled with the universal skid for facilitating the one or more unit operations.

7. The universal skid of claim 6, wherein the mean residence time of the one or more surge vessels or the plurality of flow channels is less than about 30 minutes, less than about 60 minutes, or less than about 120 minutes.

8. The universal skid of claim 1, wherein the plurality of flow-channel hardware sets comprise a plurality of sensors and a plurality of valves.

9. The universal skid of claim 1, further comprising:
a plurality of hardware components comprising one or more pumps, valves, and sensors, attached to the rigid support.

10. The universal skid of claim 1, wherein the one or more unit operations comprise one or more processing steps or one or more system components for performing, virus inactivation, virus filtration, formulation, or sterile filtration.

11. The universal skid of claim 1, further comprising a group of valves and a group of pumps for supporting and controlling the ultrafiltration or diafiltration operation, or for supporting the chromatography operation.

12. The universal skid of claim 11, further comprising at least five pumps.

13. The universal skid of claim 12, wherein at least one pump is a centrifugal pump.

14. A modular assembly for processing one or more biological products, comprising:
one or more single-use kits for one or more unit operations of a production process for the one or more biological products, the one or more single-use kits comprising one or more surge vessels and a plurality of flow channels; and
a universal skid configured to couple with the one or more single-use kits, the universal skid comprising:
a rigid support; and
a plurality of flow-channel hardware sets mounted on the rigid support, each flow-channel hardware set configured to couple with a respective flow channel of the plurality of flow channels;
wherein the plurality of flow-channel hardware sets allow for continuous processing over the one or more unit operations, and wherein the one or more single-use kits are replaceable and changeable; and
wherein at least one flow-channel hardware set of the plurality of flow-channel hardware sets includes components for supporting and controlling an ultrafiltration or diafiltration operation, and at least one flow-channel hardware set of the plurality of flow-channel hardware sets includes components supporting a chromatography operation.

15. The modular assembly of claim 14, wherein the plurality of flow-channel hardware sets each comprise at least two of the same types of hardware components as each other, providing hardware support for allowing a first flow channel associated with a first processing step of the one or more unit operations and a second flow channel associated with a second processing step of the one or more unit operations arranged in an in-parallel configuration or an in-series configuration.

16. The modular assembly of claim 14, wherein the plurality of flow-channel hardware sets allow the plurality of flow channels to operate in series for continuous processing over the one or more unit operations.

17. The modular assembly of claim 14, wherein the plurality of flow-channel hardware sets allow the plurality of flow channels to operate in parallel for continuous processing over the one or more unit operations.

18. The modular assembly of claim 14, wherein the plurality of flow-channel hardware sets reduce mean residence time in the one or more surge vessels or the plurality of flow channels.

19. The modular assembly of claim 18, wherein the mean residence time of the one or more surge vessels or the plurality of flow channels is less than about 30 minutes, less than about 60 minutes, or less than about 120 minutes.

20. The modular assembly of claim 14, wherein the unit operation comprises one or more functional steps or one or more system components for performing virus inactivation, virus filtration, formulation, or sterile filtration.

21. A manufacturing system for processing one or more biological products, comprising:
a plurality of modular assemblies coupled with each other, each modular assembly performing one or more unit operations, the plurality of modular assemblies allowing continuous processing within each of the plurality of modular assemblies, in between the plurality of modular assemblies, end-to-end continuous processing across the plurality of modular assemblies, and fully continuous processing across a plurality of unit operations, each modular assembly comprising:
one or more replaceable and changeable single-use kits for the one or more unit operations, the one or more single-use kits comprising one or more surge vessels and a plurality of flow channels; and
a universal skid configured to couple with the one or more single-use kits, the universal skid comprising:
a rigid support; and
a plurality of flow-channel hardware sets mounted on the rigid support, each flow-channel hardware set configured to couple with a respective flow channel of the plurality of flow channels,
wherein the plurality of flow-channel hardware sets allow for continuous processing over the one or more unit operations; and
wherein at least one flow-channel hardware set of the plurality of flow-channel hardware sets includes components for supporting and controlling an ultrafiltration or diafiltration operation, and at least one flow-channel hardware set of the plurality of flow-channel hardware sets includes components supporting a chromatography operation.

22. The manufacturing system of claim 21, wherein the plurality of flow-channel hardware sets each comprise at least two of the same types of hardware components as each other, providing hardware support for allowing a first flow channel associated with a first processing step of the one or more unit operations and a second flow channel associated with a second processing step of the one or more unit operations arranged in an in-parallel configuration or an in-series configuration.

23. The manufacturing system of claim 21, wherein the plurality of flow-channel hardware sets allow the plurality of flow channels to operate in series for continuous processing over the one or more unit operations.

24. The manufacturing system of claim 21, wherein the plurality of flow-channel hardware sets allow the plurality of flow channels to operate in parallel for continuous processing over the one or more unit operations.

25. The manufacturing system of claim 21, wherein an output of one modular assembly of the plurality of modular assemblies is coupled to an input of a neighboring modular assembly of the plurality of modular assemblies such that fluid continuously flows and is processed across the plurality of modular assemblies from end to end.

26. The manufacturing system of claim 21, wherein the plurality of modular assemblies have different scales to hold different liquid volumes for continuous processing.

* * * * *